United States Patent
Szczypka et al.

(10) Patent No.: US 9,029,144 B2
(45) Date of Patent: May 12, 2015

(54) METHODS FOR ENHANCED PROPAGATION OF CELLS

(75) Inventors: Mark Szczypka, Ann Arbor, MI (US); Evangelos Tziampazis, East Lyme, CT (US); Angela J. Westover, Ann Arbor, MI (US)

(73) Assignees: Innovative Bio Therapies, Inc., Ann Arbor, MI (US); CytoPherx, Inc., Ann Arbor, MI (US)

(*) Notice: Subject to any disclaimer, the term of this patent is extended or adjusted under 35 U.S.C. 154(b) by 647 days.

(21) Appl. No.: 12/485,575

(22) Filed: Jun. 16, 2009

(65) Prior Publication Data

US 2010/0136687 A1    Jun. 3, 2010

Related U.S. Application Data

(60) Provisional application No. 61/073,745, filed on Jun. 18, 2008.

(51) Int. Cl.
*C12N 5/00* (2006.01)
*C12N 5/071* (2010.01)

(52) U.S. Cl.
CPC ........ *C12N 5/0687* (2013.01); *C12N 2501/385* (2013.01)

(58) Field of Classification Search
CPC ............... C12N 5/0686; C12N 5/0687; C12N 2501/30; C12N 2501/385; A61K 35/12
USPC .......................................... 435/375, 395, 377
See application file for complete search history.

(56) References Cited

U.S. PATENT DOCUMENTS

| | | |
|---|---|---|
| 3,313,289 A | 4/1967 | Kapral |
| 3,943,936 A | 3/1976 | Rasor et al. |
| 3,952,747 A | 4/1976 | Kimmell, Jr. |
| 4,309,776 A | 1/1982 | Berguer |
| 4,332,893 A | 6/1982 | Rosenberg |
| 4,378,016 A | 3/1983 | Loeb |
| 4,393,133 A | 7/1983 | Knowles et al. |
| 4,402,694 A | 9/1983 | Ash et al. |
| 4,479,796 A | 10/1984 | Kallok |
| 4,494,531 A | 1/1985 | Gianturco |
| 4,503,569 A | 3/1985 | Dotter |
| 4,511,353 A | 4/1985 | Theeuwes |
| 4,586,922 A | 5/1986 | Theeuwes |
| 4,643,712 A | 2/1987 | Kulik et al. |
| 4,648,865 A | 3/1987 | Aigner |
| 4,655,771 A | 4/1987 | Wallsten |
| 4,673,391 A | 6/1987 | Kondo et al. |
| 4,685,918 A | 8/1987 | Amidon et al. |
| 4,771,773 A | 9/1988 | Kropf |
| 4,775,483 A | 10/1988 | Mookerjea et al. |
| 4,777,049 A | 10/1988 | Magruder et al. |
| 4,781,177 A | 11/1988 | Lebigot et al. |
| 4,793,348 A | 12/1988 | Palmaz |
| 4,793,825 A | 12/1988 | Benjamin et al. |
| 4,817,600 A | 4/1989 | Herms et al. |
| 4,820,626 A | 4/1989 | Williams et al. |
| 4,832,055 A | 5/1989 | Palestrant |
| 4,865,585 A | 9/1989 | Theeuwes |
| 4,871,352 A | 10/1989 | Tran |
| 4,877,864 A | 10/1989 | Wang et al. |
| 4,878,913 A | 11/1989 | Aebischer et al. |
| 4,892,538 A | 1/1990 | Aebischer et al. |
| 4,911,717 A | 3/1990 | Gaskill, III |
| 4,938,742 A | 7/1990 | Smits |
| 4,985,017 A | 1/1991 | Theeuwes |
| 4,994,069 A | 2/1991 | Ritchart et al. |
| 5,026,365 A | 6/1991 | Rossini et al. |
| 5,035,891 A | 7/1991 | Runkel et al. |
| 5,053,008 A | 10/1991 | Bajaj |
| 5,059,205 A | 10/1991 | El-Nounou et al. |
| 5,104,399 A | 4/1992 | Lazarus |
| 5,147,379 A | 9/1992 | Sabbaghian et al. |
| 5,152,743 A | 10/1992 | Gorsuch et al. |
| 5,152,777 A | 10/1992 | Goldberg et al. |
| 5,160,320 A | 11/1992 | Yum et al. |
| 5,164,186 A | 11/1992 | Tsuru et al. |
| 5,178,864 A | 1/1993 | Lees et al. |
| 5,182,111 A | 1/1993 | Aebischer et al. |
| 5,185,438 A * | 2/1993 | Lemischka ................ 536/23.2 |

(Continued)

FOREIGN PATENT DOCUMENTS

| | | |
|---|---|---|
| DE | 3447202 | 7/1986 |
| DE | 3941873 | 5/1991 |
| EP | 0117940 | 9/1984 |
| EP | 0341039 | 11/1989 |
| EP | 0350043 | 1/1990 |
| EP | 0560279 | 9/1993 |
| EP | 0598635 | 5/1994 |
| EP | 0604022 | 6/1994 |
| JP | 1052476 | 2/1989 |
| JP | 3502534 | 6/1991 |

(Continued)

OTHER PUBLICATIONS

Trosko et al. Oncol Res 2003;13:353-7.*
Lin et al. Clin Exp Immunol 1993;92:145-51.*
Mandl et al. Tissue Engineering 2004;10:109-18.*
Leffert et al. J Cell Biol 1972;52:559-68.*
ALZA Corporation, DUROS implant technology, http://www.alza.com, printed Jan. 7, 2002 and Mar. 18, 2005.
ALZA Corporation, DUROS technology: how does it work? http://www.alza.com, printed Jan. 7, 2002 and Jan. 13, 2005.
ALZET Osmotic Pumps—A General Description, http: www.alzet.com. Printed Jan. 7, 2002 and Jan. 13, 2005.

(Continued)

*Primary Examiner* — Janice Li
(74) *Attorney, Agent, or Firm* — Goodwin Procter LLP

(57) ABSTRACT

The present invention relates generally to methods for the isolation and propagation of cells. For example, embodiments of the present invention relate to isolation and propagation methods for the manufacture of a large number of cells for use, for example, in biotherapeutic devices, such as devices for renal replacement therapy for the treatment of acute renal failure (ARF), acute tubular necrosis (ATN), multi-organ failure (MOF), sepsis, cardiorenal syndrome (CRS) and end-stage renal disease (ESRD).

21 Claims, 20 Drawing Sheets

(56) References Cited

U.S. PATENT DOCUMENTS

| | | | |
|---|---|---|---|
| 5,200,181 A | 4/1993 | Soltys et al. | |
| 5,232,696 A | 8/1993 | Lees et al. | |
| 5,260,068 A | 11/1993 | Chen | |
| 5,282,861 A | 2/1994 | Kaplan | |
| 5,304,120 A | 4/1994 | Crandell et al. | |
| 5,314,471 A | 5/1994 | Brauker et al. | |
| 5,350,398 A | 9/1994 | Pavcnik et al. | |
| 5,360,790 A | 11/1994 | Humes | |
| 5,368,555 A | 11/1994 | Sussman et al. | |
| 5,368,588 A | 11/1994 | Bettinger | |
| 5,370,691 A | 12/1994 | Samson | |
| 5,383,887 A | 1/1995 | Nadal et al. | |
| 5,383,892 A | 1/1995 | Cardon et al. | |
| 5,383,928 A | 1/1995 | Scott et al. | |
| 5,403,917 A | 4/1995 | Boos et al. | |
| 5,411,550 A | 5/1995 | Herweck et al. | |
| 5,415,630 A | 5/1995 | Gory et al. | |
| 5,419,760 A | 5/1995 | Narciso, Jr. et al. | |
| 5,429,634 A | 7/1995 | Narciso, Jr. | |
| 5,429,938 A | 7/1995 | Humes | |
| 5,443,508 A | 8/1995 | Giampapa | |
| 5,478,807 A | 12/1995 | Cronin et al. | |
| 5,487,739 A | 1/1996 | Aebischer et al. | |
| 5,534,025 A | 7/1996 | Moussy et al. | |
| 5,549,674 A | 8/1996 | Humes et al. | |
| 5,591,230 A | 1/1997 | Horn et al. | |
| 5,609,629 A | 3/1997 | Fearnot et al. | |
| 5,649,906 A | 7/1997 | Gory et al. | |
| 5,651,174 A | 7/1997 | Schwartz et al. | |
| 5,679,775 A | 10/1997 | Boos et al. | |
| 5,681,278 A | 10/1997 | Igo et al. | |
| 5,686,289 A | 11/1997 | Humes et al. | |
| 5,696,087 A | 12/1997 | Tang et al. | |
| 5,702,717 A | 12/1997 | Cha et al. | |
| 5,704,910 A | 1/1998 | Humes | |
| 5,713,853 A | 2/1998 | Clark et al. | |
| 5,720,764 A | 2/1998 | Naderlinger et al. | |
| 5,722,992 A | 3/1998 | Goldmann et al. | |
| 5,733,327 A | 3/1998 | Igaki et al. | |
| 5,735,897 A | 4/1998 | Buirge | |
| 5,756,291 A | 5/1998 | Griffin et al. | |
| 5,773,327 A | 6/1998 | Yamazaki et al. | |
| 5,788,468 A | 8/1998 | Dewa et al. | |
| 5,788,673 A | 8/1998 | Young et al. | |
| 5,797,887 A | 8/1998 | Rosen et al. | |
| 5,797,898 A | 8/1998 | Santini, Jr. et al. | |
| 5,800,421 A | 9/1998 | Lemelson | |
| 5,810,767 A | 9/1998 | Klein | |
| 5,834,449 A | 11/1998 | Thompson et al. | |
| 5,843,781 A | 12/1998 | Ballermann et al. | |
| 5,855,892 A | 1/1999 | Potter et al. | |
| 5,873,904 A | 2/1999 | Ragheb et al. | |
| 5,876,446 A | 3/1999 | Agrawal et al. | |
| 5,891,154 A | 4/1999 | Loeffler | |
| 5,895,407 A | 4/1999 | Jayaraman et al. | |
| 5,899,935 A | 5/1999 | Ding | |
| 5,902,336 A | 5/1999 | Mishkin | |
| 5,911,704 A | 6/1999 | Humes | |
| 5,964,745 A | 10/1999 | Lyles et al. | |
| 5,981,252 A | 11/1999 | MacPhee et al. | |
| 6,017,362 A | 1/2000 | Lau | |
| 6,022,333 A | 2/2000 | Kensey | |
| 6,027,516 A | 2/2000 | Kolobow et al. | |
| 6,027,520 A | 2/2000 | Tsugita et al. | |
| 6,030,336 A | 2/2000 | Franchi et al. | |
| 6,030,414 A | 2/2000 | Taheri | |
| 6,036,725 A | 3/2000 | Avellanet | |
| 6,056,734 A | 5/2000 | Jacobsen et al. | |
| 6,059,825 A | 5/2000 | Hobbs et al. | |
| 6,060,270 A | 5/2000 | Humes | |
| 6,071,035 A | 6/2000 | McKelvy | |
| 6,080,178 A | 6/2000 | Meglin | |
| 6,093,199 A | 7/2000 | Brown et al. | |
| 6,099,495 A | 8/2000 | Kinghorn et al. | |
| 6,099,864 A | 8/2000 | Morrison et al. | |
| 6,106,454 A | 8/2000 | Berg et al. | |
| 6,113,608 A | 9/2000 | Monroe et al. | |
| 6,113,621 A | 9/2000 | Wiktor | |
| 6,126,673 A | 10/2000 | Kim et al. | |
| 6,129,757 A | 10/2000 | Weadock | |
| 6,132,458 A | 10/2000 | Staehle et al. | |
| 6,136,011 A | 10/2000 | Stambaugh | |
| 6,150,164 A | 11/2000 | Humes | |
| 6,283,951 B1 | 9/2001 | Flaherty et al. | |
| 6,290,728 B1 | 9/2001 | Phelps et al. | |
| 6,410,320 B1 | 6/2002 | Humes | |
| 6,440,734 B1 | 8/2002 | Pykett et al. | |
| 6,491,666 B1 | 12/2002 | Santini, Jr. et al. | |
| 6,548,299 B1 | 4/2003 | Pykett et al. | |
| 6,561,997 B1 | 5/2003 | Weitzel et al. | |
| 6,572,605 B1 | 6/2003 | Humes | |
| 6,585,756 B1 | 7/2003 | Strecker et al. | |
| 6,645,489 B2 | 11/2003 | Pykett et al. | |
| 6,653,131 B2 | 11/2003 | Humes | |
| 6,673,339 B1 * | 1/2004 | Atala et al. | 424/93.2 |
| 6,716,208 B2 | 4/2004 | Humes | |
| 6,913,588 B2 | 7/2005 | Weitzel et al. | |
| 6,942,879 B2 | 9/2005 | Humes | |
| 6,991,933 B1 | 1/2006 | Upton et al. | |
| 7,192,769 B2 | 3/2007 | Pykett et al. | |
| 7,332,330 B2 | 2/2008 | Humes et al. | |
| 7,442,546 B2 | 10/2008 | Humes | |
| 2001/0041363 A1 | 11/2001 | Humes | |
| 2002/0090388 A1 | 7/2002 | Humes et al. | |
| 2002/0090389 A1 | 7/2002 | Humes et al. | |
| 2002/0119566 A1 | 8/2002 | Humes | |
| 2004/0096430 A1 | 5/2004 | Bauer | |
| 2005/0019370 A1 | 1/2005 | Humes | |
| 2005/0238687 A1 | 10/2005 | Humes | |
| 2006/0019362 A1 | 1/2006 | Yu et al. | |
| 2006/0084170 A1 | 4/2006 | Pykett et al. | |
| 2006/0177478 A1 | 8/2006 | Humes et al. | |
| 2006/0194310 A1 | 8/2006 | Upton et al. | |
| 2006/0286078 A1 | 12/2006 | Humes | |
| 2007/0065942 A1 | 3/2007 | Wandinger-Ness et al. | |
| 2007/0269489 A1 | 11/2007 | Humes | |
| 2009/0060890 A1 | 3/2009 | Humes et al. | |
| 2009/0081296 A1 | 3/2009 | Humes et al. | |
| 2009/0130756 A1 | 5/2009 | Klann et al. | |

FOREIGN PATENT DOCUMENTS

| | | |
|---|---|---|
| WO | WO-89/04655 | 6/1989 |
| WO | WO-90/06997 | 6/1990 |
| WO | WO-92/15676 | 9/1992 |
| WO | WO-93/06878 | 4/1993 |
| WO | WO-93/17696 | 9/1993 |
| WO | WO-94/15583 | 7/1994 |
| WO | WO-95/00654 | 1/1995 |
| WO | WO-95/11048 | 4/1995 |
| WO | WO-96/14397 | 5/1996 |
| WO | WO-96/14399 | 5/1996 |
| WO | WO-96/39098 | 12/1996 |
| WO | WO-97/12680 | 4/1997 |
| WO | WO-99/15629 | 4/1999 |
| WO | WO-99/48545 | 9/1999 |
| WO | WO-99/55360 | 11/1999 |
| WO | WO-99/63971 | 12/1999 |
| WO | WO-00/27999 | 5/2000 |
| WO | WO-00/64510 | 11/2000 |
| WO | WO-01/21760 | 3/2001 |
| WO | WO-01/21766 | 3/2001 |
| WO | WO-02/055136 | 7/2002 |
| WO | WO-02/056796 | 7/2002 |
| WO | WO-03/020104 | 3/2003 |
| WO | WO-03/022125 | 3/2003 |
| WO | WO-03/077840 | 9/2003 |
| WO | WO-03/095603 | 11/2003 |
| WO | WO-03/100010 | 12/2003 |
| WO | WO-2006/138537 | 12/2006 |
| WO | WO-2007/092735 | 8/2007 |
| WO | WO-2008/045498 | 4/2008 |

(56) References Cited

FOREIGN PATENT DOCUMENTS

| WO | WO-2009/029801 | 3/2009 |
|---|---|---|
| WO | WO-2010/019643 | 2/2010 |
| WO | WO-2010/071692 | 5/2010 |

OTHER PUBLICATIONS

Acchiardo et al. (1989) "$\beta_2$-Microglobulin Levels in Patients With Renal Insufficiency," American Journal of Kidney Diseases, 13(1):70-74.

Aebisher et al. (1991) "Transplantation of Microencapsulated Bovine Chromaffin Cells Reduces Lesion-induced Rotational Assymetry in Rats," Brain Research 560: 43-49.

Albert et al. (1992) "Evaluation of Various Gene Transfection Methods Into Human Myoblast Clones," Transportation Proceedings 24: 2784-2786.

Arosop e al. (1993) "Effects of Sustained-Release Isradipine on Blood Pressure and Peripheral Hemodynamics in Hypertensive Patients," Clin Ther 15(4):705-13.

Badesch et al. (2000) "Continuous Intravenous Epoprostenol for Pulmonary Hypertension Due to Scleroderma Spectrum of Disease," Annals of Internal Medicine. 132(6):425-434.

Berner et al (1992) "Fundamental Concepts in Controlled Release," in Treatise on Controlled Drug Delivery (Kydonieus Ed), Marcel Dekker, Inc., New York, pp. 1, 14-15.

Buerk et al. (1982) "Arterial Wall Oxygen Consumption Rate Varies Spatially," Am. J. Physiol., 243(6):H948-58.

Cesario et al. (1998) "Beneficial Effects of Intermittent Home Administration of the Inotrope/Vasodilator Milrinone in Patients with End-Stage Congestive Heart Failure: A Preliminary Study," American Heart Journal, 135(1):121-129.

Craig (1993) "Outpatient Parenteral Antibiotic Therapy. Management of Serious Infections. Part I: Medical, Socioeconomic, and Legal Issues. Selecting the Antibiotic," Hosp. Pract. (Off. Ed.) Suppl. (1): 16-20.

Crystal (1992) "Gene Therapy Strategies for Pulmonary Disease," The American Journal of Medicine 92: 6A-44S-6A-52S.

Danos et al. (1988) "Safe and Efficient Generation of Recombinant Retroviruses with Amphotropic and Ecotropic Host Rangers," Proc. Natl. Acad. Sci., 85:6460-6464.

Deedwania et al. (1998) "Spontaneous Conversion and Maintenance of Sinus Rhythm by Amiodarone in Patients with Heart Failure and Atrial Fibrillation—Observations from the Veterans Affairs Congestive Heart Failure Survival Trial of Antiarrhythmic Therapy (CHF-STAT)," Circulation, 98:2574-2579.

Dranoff et al. (1993) "Vaccination with Irradiated Tumor Cells Engineered to Secrete Murine Granulocyte-Macrophage Colony-Stimulating Factor Stimulated Potent, Specific, and Long-Lasting Antitumor Immunity," Proc Natl. Acad. Sci., 90:3539-3543.

Durack (1993) "Outpatient Parenteral Antibiotic Therapy. Management of Serious Infections. Part II Amenable Infections and Models for Delivery. Endocarditis," Hosp. Pract. (Off. Ed.) Suppl. (2):6-9.

Dwarki et al. (1995) "Gene Therapy for Hemophilia A: Production of Therapeutic Levels of Human Factor VIII in vivo in Mice," Proc Natl. Acad. Sci. USA 92: 1023-1027.

Edelman et al. (1995) "c-myc in Vasculoproliferative Disease," Circulation Research, 76(2): 176-182.

Gage (1998) "Cell Therapy," Nature, 392:18-24.

Garver et al. (1967) "Clonal Gene Therapy: Transplanted Mouse Fibroblast Clones Express Human $\alpha$1-Antitrypsin Gene in Vivo," Science 237: 762-764.

Gibaldi, ed. (1991) "Nonoral Medication," in Biopharmaceutics and Clinical Pharmacokinetics, Lea & Febiger, 4th Edition, Philadelphia, pp. 80-123.

Ginsberg (1994) "Lipoprotein Metabolism and its Relationship to Atherosclerosis," Medical Clinics of North America, 78(1):1-20.

Glaser (1995) "Bioreactor Innovations Focus on Control, Cell Density & Cost Efficiency," Genetic Engineering News Feb. 1, 1995.

Goldberg et al. (1987) "The Regulated Expression of Erythropoietin by Two Human Hepatoma Cell Lines" Proc. Natl. Acad. Sci. USA 84: 7972-7976.

Golomb, et al (1998) "Controlled Delivery of a Tyrphostin Inhibits Intimal Hyperplasia in a Rat Carotid Artery Injury Model," Atherosclerosis, 125:171-82.

Greenfield et al. (1973) "A New Intracaval Filter Permitting Continued Flow and Resolution of Emboli," Surgery 73:599-606.

Greenfield et al. (1977) "Clinical Experience with the Kim-Ray Greenfield Vena Caval Filter," Ann. Surg. 185: 692-698.

Greenfield (1981) "Greenfield Vena Caval Filter Experience," Arch Surg 116 1451-1456.

Greenfield (1991) "Venous Thromboembolic Disease," Chapter 37 in "Vascular Surgery, A Comprehensive Review," Moore, Ed, pp. 669-679.

Hamamori et al. (1995) "Myoblast Transfer of Human Erythropoietin Gene in Mouse Model of Renal Failure," J. Clin. Invest 95: 1808-1813.

Harjai et at, (1997) "Home Inotropic Therapy in Advanced Heart Failure, Cost Analysis and Clinical Outcomes," Chest, 112(5):1298-1303.

Haskel et al. (1991) "Relative Efficacy of Antithrombin Compared with Antiplatelet Agents in Accelerating Coronary Thrombolysis and Preventing Early Reocclusion," Circulation: 83:1048-1056.

Heeschen et al. (1999) "Troponin Concentrations for Stratification of Patients with Acute Coronary Syndromes in Relation to Therapeutic Efficacy of Tirofiban," Lancet. 354:1757-62.

Heras et al. (1990) "Hirudin, Heparin, and Placebo During Deep Arterial Injury in the Pig. The in Vivo Role of Thrombin in Platelet-Mediated Thrombosis," Circulation, 82:1476-1484.

Higenbottam et al. (1998) "Treatment of Pulmonary Hypertension with the Continuous Infusion of a Prostacyclin Analogue, Iloprost," Heart, 79:175-179.

Hjalmarson et al. (2000) "Effects of Controlled-Release Metoprolol on Total Mortality, Hospitalizations, and Well-being in Patients with Heart Failure," JAMA, 283 (10):1295-1302.

Hoeben et al. "Toward Gene Therapy in Haemophilia A: Retrovirus-Mediated Transfer of a Factor VIII Gene into Murine Haematopoietic Progenitor Cells," Thromb Haemost., 1992, vol. 67, 341-5.

Hsu (1991) "Principles of Heparin-Coating Techniques," Perfusion, 6:209-219.

Irori (1997) Class A96, AN 1997-226007, XP002201866 & WO 97 12680 A, Database WPI Section Ch, week 199720, Derwent Publications Ltd., London, GB.

Jelkmann, W. (1992) "Erythropoietin: Structure, Control of Production, and Function," Physiological Reviews 72: 449-489.

Kato et al. (1984) "Magnetic Microcapsules for Targeted Delivery of Anticancer Drugs," Appl Biochem Biotechnol 10:199-211.

Kaukinen et al. (1985) "Clinical Study on ZK 36 374: A New Stable Prostacyclin Analog for Treatment of Peripheral Vascular Disease," Prostacyclin-Clinical Trials (Gryglewski et al. Eds.) Raven Press, New York, pp. 23-29.

Kravitz (1993) "Outpatient Parenteral Antibiotic Therapy. Management of Serious Infections. Part I: Medical, Socioeconomic, and Legal Issues. Advances in IV Delivery," Hosp. Pract. (Off. Ed.) Suppl. (1):21-27.

Kroon, et al. (1999) "The Rebound of Lipoproteins after LDL-Apheresis. Effects on Chemical Composition and LDL-Oxidizability," Atherosclerosis, 147:105-113.

Kurachi at al. (1993) "Gene Therapy of Hemophilia B," Thromb. Haemost., 70: 193-197.

Labeque et al. (1993) "Enzymatic Modification of Plasma Low Density Lipoproteins in Rabbits: A Potential Treatment for Hypercholesterolemia," Proc. Natl. Acad. Sci, USA 90:3478-3480.

Labhasetwar et al. (1994) "Sotalol Controlled-Release Systems for Arrhythmias: in Vitro Characterization, in Vivo Drug Disposition, and Electrophysiologic Effects," J Pharm Sci 83(2):156-64.

Labhasetwar et al. (1998) "Prevention of Acute Inducible Atrial Flutter in Dogs by Using an Ibutilide-Polymer-Coated Pacing Electrode," J Cardiovasc Pharmacol, 31(3):449-55.

(56) References Cited

OTHER PUBLICATIONS

Labhasetwar et al. (1994) "Epicardial Administration of Ibutilide from Polyurethane Matrices: Effects on Defibrillation Threshold and Electrophysiologic Parameters," J Cardiovesc Pharmacol 24(5),828-40.
Labhasetwar et al. (1998) "A DNA Controlled-Release Coating for Gene Transfer Transfection in Skeletal and Cardiac Muscle," J Pharm Sci 87(11):1347-50.
Lacy et al. (1976) "Long-term Perfusion of Isolated Rat Islets in Vitro," Diabetes 25: 484-493.
Langer (1998) "Drug Delivery and Targeting," Nature 392:5-10.
Lehmann et al. (1995) "Haemodynamic Evaluation of Two Regimens of Molsidomine in Patients with Chronic Congestive Heart Failure" Eur. J. Clin. Pharmacol. 48:109-114.
Li et al. (1987) "Influence of Drug Properties and Routes of Drug Administration on the Design of Sustained and Controlled Release Systems," in Controlled Drug Delivery (Robinson et al. Eds.), 2nd Ed., Marcel Dekker, Inc., New York, Chapter 1, pp. 36-38.
Liguori et al. (1999) "Loop Diuretics Enhance the Secretion of Prostacyclin In Vitro, in Healthy Persons, and In Patients with Chronic Heart Failure," Eur. J. Clin. Pharmacol. 55: 117-124.
Lozier, et al. (1994) "Gene Therapy and the Hemophilias," JAMA 271(1): 47-51.
Malchesky et al. (1993) "Are Selective Macromolecule Removal Plasmapheresis Systems Useful for Autoimmune Diseases or Hyperlipidemia?" ASAIO J. 39: 868-72.
Mandell, Douglas, and Bennett's Principles of and Practice of Infectious Diseases, Fourth Edition (1979), Chapter 12 Principles of Anti-Infective Therapy pp. 209.
Masuyama et al. (1990) "Effects of Nitroprusside on Transmitral Flow Velocity Patterns in Extreme Heart Failure: A Combined Hemodynamic and Doppler Echocardiographic Study of Varying Loading Conditions," JACC 16:1175-85.
Maxwell et al. (1993) "Identification of the Renal Erythropoietin-producing Cells Using Transgenic Mice." Kidney International 44: 1149-1162.
Meyer et al. (1994) "Local Delivery of r-Hirudin by a Double-Balloon Perfusion Catheter Prevents Mural Thrombosis and Minimizes Platelet Deposition After Angioplasty," Circulation, 90:2474-2480.
Muller et al. (1996) "Sustained-Release Local Hirulog Therapy Decreases Early Thrombosis But Not Neointimal Thickening After Arterial Stenting," Am Heart J 131(2):211-8.
Nashitz et al. (1993) "Thromboembolism in Cancer," Cancer 71: 1384-1390.
Odell et al. (1991) "Beta$_2$-Microglobulin Kinetics in End-Stage Renal Failure," Kidney International 39:909-919.
Oliva et al. (1999) "Intermittent 6-Month Low-Dose Dobutamine Infusion in Severe Heart Failure: DICE Multicenter Trial," American Heart Journal 138(2):247-53.
Orloff et al. (1995) "Prevention of Venous Thrombosis in Microvascular Surgery by Transmural Release of Heparin from a Polyanhydride Polymer," Surgery 117(5):554-59.
Racz et al. (1986) "Stability Study of Prostacyclin in Solution," Pharmazie 41 (H.11):769-771.
Revillard et al. (1998) "Structure and Metabolism of Beta-2-Microglobulin," Contr. Nephrol. 62:44-53.
Rogers et al. (1993) "Inhibition of Experimental Neointimal Hyperplasia and Thrombosis Depends on the Type of Vascular Injury and the Site of Drug Administration," Circulation 88(3):1215-21.
Roman et al. (1992) "Circulating Human or Canine Factor IX from Retrovirally Transduced Primary Myoblasts and Established Myoblast Cell Lines Grafted into Murine Skeletal Muscle," Somatic Cell and Molecular Genetics 18: 247-258.
Sanaka et al. (1989) "Extracorporeal Hybridization of Proximal Renal Tubular Cells and an Artificial Membrane for the Purpose of Beta$_2$ Microglobulin Removal," Trans. Am. Soc. Artif. Intern. Organs 35:527-530.
Shapiro et al. (1997) "Primary Pulmonary Hypertension: Improved Long-Term Effects and Survival with Continuous Intravenous Epoprostenol Infusion," JACC 30:343-9.
Shefer et al. (1993) "Extracorporeal Enzymatic Removal of Low Density Lipoproteins in Rabbits: Efficacy and Safety," Int. J. Artif. Organs 16 (4):218-28.
Siden et al. (1992) "Epicardial Propranolol Administration for Ventricular Arrhythmias in Dogs: Matrix Formulation and Characterization," Biomaterials 13(11):764-70.
Sindone et al (1997) "Continuous Home Ambulatory Intravenous Inotropic Drug Therapy in Severe Heart Failure: Safety and Cost Efficacy," American Heart Journal 134(5):889-900.
Skuballa et al. (1987) "Chemistry of Stable Prostacyclin Analogues: Synthesis of Iloprost," Prostacyclin and Its Stable Analogue Iloprost (Gryglewski et al. Ed.) Springer-Verlag, Berlin Heidelberg, Germany, pp. 17-24.
Thompson et al. (1995) "Familial Hyoercholesterolaemia Regression Study: A Randomised Trial of Low-Density-Lipoprotein Apheresis," Lancet, 345:811-16.
Tice (1993) "Introduction," Proceedings of a Symposium held on Jan. 26 and 27, 1993, Sonoma, California, 1 pg.
Tice (1993) "Outpatient Parenteral Antibiotic Therapy. Management of Serious Infections. Part II: Amenable Infections and Models for Delivery, Osteomyelitis," Hosp. Pract. (Off Ed.) Suppl (2):36-9, discussion 60-1.
Tripathy et al. (1994) "Stable Delivery of Physiologic Levels of Recombinant Erythropoietin to the Systemic Circulation by Intramuscular Injection of Replication-defective Adenovirus," Proc. Natl. Acad. Sci. USA 91: 11557-11561.
Tong et al. (1992) "Non-thrombogenic Hemofiltration System for Acute Renal Failure Treatment," ASAIO J. M702-M706.
Waller (1999) "Optimal Nitrate Therapy with a Once-Daily Sustained-Release Formulation of Isosorbide Mononitrate," J Cardiovasc Pharmacol 34 (suppl. 2): S21-7.
Wollheim et al. (1990) "Establishment and Culture of Insulin-Secreting β Cell Lines," Methods in Enzymology, 192: 223-235.
Wollheim et al. (1990) "Isolation of Pancreatic Islets and Primary Culture of the Intact Microorgans or of Dispersed Islet Cells," Methods in Enzymology, 192: 188-223.
Yamamura et al. (1995) "Sustained Release of Basic Fibroblast Growth Factor from the Synthetic Vascular Prosthesis Using Hydroxypropylchitosan Acetate," J Biomed Mater Res 29(2): 203-6.
Yao et al. (1992) "Expression of human factor IX in mice after injection of genetically modified myoblasts," Proc. Natl. Acad. Sci. USA 89 3357-3361.
Yao et al. (1993) "Implanted Myoblasts Not Only Fuse With Myofibers But Also Survive As Muscle Precursor Cells," Journal of Cell Science 105: 957-963.
Yao et al. (1994) "Primary Myoblast-mediated Gene Transfer: Persistent Expression of Human Factor IX in Mice." Gene Therapy 1: 99-107.
Yu et al. (1998) "The Biologic Effects of Growth Factor—Toxin Conjugates in Models of Vascular Injury Depend on Dose, Mode of Delivery, and Animal Species," J Pharm Sci, 87(11): 1300-4.
Buffington et al. (Apr. 6, 2008, submission date) NIH Small Business Innovation Research Proposal Phase II submission, Abstract provided (3 pages).
Buffington et al. (Apr. 6. 2008, submission date) NIH Small Business Innovation Research Proposal Phase I submission, Abstract provided (3 pages).
Humes et al. (Feb. 16, 2007, submission date) "Nanofabricated Bioartificial Kidney," U.S. Army Med. Research and Materiel Command, Grant No. W81XWH-05-2-0010, P00005, FY05 Modification, Abstract provided.
Humes et al. (Mar. 16, 2007, submission date) "Nanofabricated Bioartificial Kidney," U.S. Army Med. Research and Materiel Command, Grant No. W81XWH-05-2-0010, P00005, FY06 Modification, Abstract provided.
Humes, et al. (Oct. 30, 2007, submission date) "Nanofabricated Bioartificial Kidney," U.S. Army Med. Research and Materiel Command, Grant No. W81XWH-05-2-0010, FY07 Modification, Abstract provided.
Buffington (May 2, 2008, project start date) "Cell Therapy for Septic Shock," National Institute of Diabetes and Digestive and Kidney Diseases, Grant No. 1R43DK074289-01, Abstract provided.

(56) References Cited

OTHER PUBLICATIONS

Buffington (May 2, 2006, project start date) "Cell Therapy for Septic Shock," National Institute of Diabetes and Digestive and Kidney Diseases, Grant No. 5R430K074289-02, Abstract provided.
Buffington (May 2, 2008, project start date) "Cell Therapy far Septic Shock," National Institute of Diabetes and Digestive and Kidney Diseases, Grant No. 2R44DK074289-03, Abstract provided.
International Search Report for Application No. PCT/US2007/061468, mailed Oct. 9, 2008 (2 pages).
Fissell, et al. (2002) "Bioartificial Kidney Alters Cytokine Response and Hemodynamics in Endotoxin-Challenged Uremic Animals," Blood Purif. 20: 55-60.
Fissell, et al. (2003) "Bioartificial Kidney Ameliorates Gram-Negative Bacteria-Induced Septic Shock in Uremic Animals," J. Am. Soc. Nephrol. 14: 454-461.
Greenfield, et al. "Venous Interruption," Ch. 68, pp. 929-940 in "Hamimovic's Vascular Surgery Principles and Techniques," Third Edition, Appleton and Lange, Norwalk, CT/San Mateo, CA.
Humes, et al. (2003) "Cell Therapy with a Tissue-Engineered Kidney Reduces the Multiple-Organ Consequences of Septic Shock," Crit. Care Med., 31(10): 2421-2428.
Humes, et al. (2004) "Initial Clinical Results of the Bioartificial Kidney Containing Hunan Cells in ICU Patients with Acute Renal Failure," Kidney Int'l 66: 1578-1588.
Humes, et al (2002) "Metabolic Replacement of Kidney Function in Uremic Animals with a Bioartificial Kidney Containing Human Cells," Am. J. of Kidney Dis 39(5): 1078-1087.
Humes, et al. (1999) "Replacement of Renal Function in Uremic Animals with a Tissue-Engineered Kidney," Nature BlOtechnolcgy, 17: 451-455.
Humes, et al. (1999) "Tissue engineering of a bioartificial renal tubule assist device: In vitro transport and metabolic characteristics," Kidney International 55: 2502-14.
Marty, et al. (1994) "Circulating interleukin-8 concentrations in patients with multiple organ failure of septic and nonseptic origin," Critical Care Medicine, 22(4): 673-79.
Pinsky, et al. (1993) "Serum cytokine levels in human septic shock. Relation to multiple-stem organ failure and mortality," Chest 1993, 103: 565-75.
Radovich (1995) "Composition of Polymer Membranes for Therapies of End-Stage Renal Disease," Dialysis Membranes. Structure and Predictions. Contrib. Nephrol., Basel Karger 113: 11-24.
Tumlin, et al. (2005) "Effect of the Renal Assist Device (RAD) on Mortality of Dialysis-Dependent Acute Renal Failure: A Randomized, Open-Labeled, Multicenter, Phase II Trial," J. Am. Soc Nephrol. 16: 46A, abstract.
Williams, et al. (2006) "Renal Bioreplacement Therapy (RBT) Reduces Mortality in ICU Patients with Acute Renal failure (ARF)," Abstract.
Agrawal, et al. (2004) "Water Distribution Studies within Microcystalline Cellulose and Chitosan Using Differential Scanning Calorimetry and Dynamic Vapor Sorption Analysis," J Pharm Sci 93(7): 1766-1779.
Barbucci, et al. (2002) "Dependence of Water Uptake and Morphology of Hyaluronan- and Alginate-Based Hydrogels on pH and Degree of Crosslinking," Macromol. Chem. Phys. 203: 1292-1300.
Brockbank, et al. (2007) "Cryopreservation Guide," Thermo Scientific white paper, pp. iii-v, 1-24.
Kim et al. (2005) "Nephrogenic Factors Promote Differentiation of Mouse Embryonic Stem Cells into Renal Epithelia," Am. Soc. Nephrol. 16(12): 3527-3534.
Fahy, et al. (2006) "Cryopreservation of Complex Systems: The Missing Link in Regenerative Chain," Rejuvenation Research 9(2): 279-291.
Mazur (1970) "Cryobiology: The Freezing of Biological Systems," Science 168 (934): 939-49.
Mazur (1984) "Freezing of Living Cells: Mechanisms and Implications," Am J. Physiol 247: C125-C142.
International Search Report for PCT/US2009/047522 mailed on Jul. 14, 2010 (4 pages).

Canaple, et al. (2001) "Maintenance of Primary Murine Hepatocyte Functions in Multicomponent Polymer Capsules—in Vitro Cryopreservation Studies," Journal of Hepatology 34: 11-18.
Itle, et al. (2005) "Cryopreservation of Cell-Containing Poly(ethylene) Glycol Hydrogel Microarrays," Biotechnol. Prog. 21: 1004-1007.
Kofron, et al. (2003) "Cryopreservation of Tissue Engineered Constructs for Bone," J. Orthop Res., (6): 1005-10. (Abstract).
Liu, et al. (2007) "Freezing Osteoblast Cells Attached to Hydroxyapatite Discs and Glass Coverslips: Mechanisms of Damage," Science in China Series E: Technological Sciences, 248-256.
Liu, et al., (2002) "Response of Murine Osteoblasts and Porous Hydroxyapatite Scaffolds to Two-Step, Slow Freezing and Vitrificaton Processes," Cell Preservation Technology 1(1): 33-44. (Abstract).
Liu, et al. (2004) "Vitrification Solutions for the Cryopreservation of Tissue-Engineered Bone," Cell Preservation Technology 2: 133-143.
Malpique, et al. (2010) "Alginate Encapsulation as a Novel Strategy for the Cryopreservation of Neurospheres," Tissue Engineering, 1-13.
Pegg (2002) "Cryopreservation of Vascular Endothelial Cells as Isolated Cells and as Monolayers," Cryobiology, 44(1): 46-53. (Abstract).
Vrana, et al. (2009) "Cell Encapsulation Within PVA-Based Hydrogels Via Freeze-Thawing: A One-Step Scaffold Formation and Cell Storage Technique," Journal of Tissue Engineering and Regenerative Medicine 3: 567-572.
Tumlin, et al. (2008) "Efficacy and Safety of Renal Tubule Cell Therapy for Acute Renal Failure," Am Soc Nephrol 19(5): 1034-40. (Abstract).
Wu, et al. (2004) "Glutathione Metabolism and its Implications for Health," J Nutr. 134(3): 489-92. (Abstract).
Corning Incorporated (printed in 2009) "Cryogenic Preservation and Storage of Animal Cells," Life Sciences, 1-5.
International Search Report for PCT/US2009/053516 mailed on Apr. 12, 2010 (4 pages).
Chertow, et al (1998) "Independent Association Between Acute Renal Failure and Mortality Following Cardiac Surgery," Am. J. Med. 104(4): 343-348.
Bates, et al. (2001) "Mortality and Costs of Acute Renal Failure Associated with Amphotericin B Therapy," Clin. Infect. Dis. 32(5): 686-693.
Humes (1995) "Acute renal failure: Prevailing challenges and prospects for the future," Kidney Int. 48:S26-S32.
Schrier, et al. (2004) "Acute Renal Failure and Sepsis," N. Engl. J. Med. 351(2): 159-169.
Shlipak, et al (2004) "The Clinical Challenge of Cardiorenal Syndrome," Circulation, 110(12): 1514-1517.
Gottlieb, et al. (2002) "The Prognostic Importance of Different Definitions of Worsening Renal Function in Congestive Heart Failure," J. Card. Fail., 8(3):136-141.
Fonarow, et al. (2005)"Risk Stratification for In-Hospital Mortality in Acutely Decompensated Heart Failure: Classification and Regression Tree Analysis," JAMA, 293(5): 572-580.
Iglehart (1993) "The American Health Care System. The End Stage Renal Disease Program," N. Engl. J. Med., 328(5): 366-371.
"V. Patient Mortality and Survival," Excerpts from United States Renal Data System: Annual Data Report (1998) Am. J. Kidney Dis. 32(2). Suppl. 1:S69-S80.
Xue, et al. (2001) "Forecast of the Number of Patients with End-Stage Renal Disease in the United States to the Year 2010," J. Am. Soc. Nephrol. 12(12): 2753-8.
Cukor, et al. (2007) "Psychosocial Aspects of Chronic Disease: ESRD as a Paradigmatic Illness," J. Am. Soc. Nephrol. 18(12):3042-3055.
Collins, et al. (2005) "Excerpts from the United States Renal Data System 2004 annual data report: atlas of end-stage renal disease in the United States," Am. J. Kidney Dis. 45(1) (Suppl. 1): Av-vii.
Humes, et al. (2003) "Renal Cell Therapy is Associated with Dynamic and Individualized Response in Patients with Acute Renal Failure," Blood Purif. 21(1):64-71.

(56) References Cited

OTHER PUBLICATIONS

Fahy, et al, (2004) "Improved Vitrification Solutions Based on the Predictability of Vitrification Solution Toxicity," Cryobiology 48: 22-35.
Gibson-D'Ambrosio et al. (1987) "Characteristics of Long-Term Human Epithelial Cell Cultures Derived from Normal Human Fetal Kidney," In Vitro Cellular & Developmental Biology 23(4):279-287.
Al-Awqati et al. "The kidney papilla is a stem cells niche" (2006), Stem Cell Rev. 2(3):181-4.
Bi et al. "Stromal cells protect against acute tubular injury via an endocrine effect" (2007), J. Am. Soc. Nephrol. 18(9):2486-96.
Challen et al. "Kidney side population reveals multilineage potential and renal functional capacity but also cellular heterogeneity" (2006). J. Am. Soc. Nephrol. 17(7):1896-912.
Duffield et al. "Kidney tubular epithelium is restored without replacement with bone marrow-derived cells during repair after ischemic injury" (2005), Kidney Int. 68(5):1956-61.
Gupta et al. "A role for extrarenal cells in the regeneration following acute renal failure" (2002), Kidney Int. 62(4):1285-90.
Hall et al. "Stem cells: the generation and maintenance of cellular diversity" (1989), Development 106:619-633.
Herrera et al. "Mesenchymal stem cells contribute to the renal repair of acute tubular epithelial injury" (2004), Int. J. Mol. Med. 14(6):1035-41.
Humes et al. "Interaction between growth factors and retinoic acid in the induction of kidney tubulogenesis in tissue culture" (1992), Exp. Cell Res. 201:8-15.
Imai et al., (2007), "The Continuing Story of Renal Repair with Stem Cells," J. Am. Soc. Nephrol. 18:2423-2428.
Kale et al. (2003), "Bone marrow stem cells contribute to repair of the ischemically injured renal tubule" J. Clin. Invest. 112:42-49.
Potten et al. "Stem cells: attributes, cycles, spirals, pitfalls and uncertainties. Lessons for and from the crypt" (1990), Development 110:1001-1020.
Poulsom et al. "Bone marrow contributes to renal parenchymal turn-over and regeneration" (2001), J. Pathol. 195:229-235.
Smith et al. (2006), "Kidney epithelial cells" Methods Enzymol. 419:194-207.

\* cited by examiner

| Porcine RBC Isolation | Historical Method (Cell Yield/Gram Kidney Cortex) | Enhanced Propagation Method (1:16) (Cell Yield/Gram Kidney Cortex) | Increase in Yield | Additional Cell Doublings | Devices/Kidney ($10^9$ cells/device) |
|---|---|---|---|---|---|
| 0 | 1.39E+09 | 1.34E+16 | 9,640,288 X | 23.2 | 2,546,000,000 |

Figure 10

| Human REC Isolation | Historical Method (Cell Yield/Gram Kidney Cortex) | Enhanced Propagation Method (L16) (Cell Yield/Gram Kidney Cortex) | Increase in Yield | Additional Cell Doublings | Devices/Kidney ($10^9$ cells/device) |
|---|---|---|---|---|---|
| A | 6.82E+07 | 9.21E+10 | 1,350 X | 10.4 | 82,890 |
| B | 1.26E+07 | 3.75E+10 | 2,976 X | 11.5 | 16,688 |
| C* | 1.00E+08 | 9.20E+16 | 920,000,000 X | 29.8 | 80,960,000,000 |
| D | 4.28E+07 | 8.84E+11 | 20,654 X | 14.3 | 566,644 |
| E | 5.32E+07 | 3.22E+10 | 605 X | 9.2 | 28,980 |
| F | N/A | Cells remain in expansion culture. Punch biopsy minced on this kidney. | | | |
| F (Punch Biopsy Through Passage 4) | N/A | 1.13E+10 | Units/11 mg biopsy | | 1 |

*no known renal disease

Figure 24

METHODS FOR ENHANCED PROPAGATION OF CELLS

REFERENCE TO RELATED APPLICATIONS

This application claims the benefit of and priority to U.S. Patent Application Ser. No. 61/073,745, filed Jun. 18, 2008, the entire disclosure of which is incorporated by reference herein.

STATEMENT REGARDING FEDERALLY SPONSORED RESEARCH OR DEVELOPMENT

This invention was sponsored, in part, by the U.S. Army Medical Research and Materiel Command, contract number W81XWH-05-2-0010 and by the SBIR program of the National Institutes of Health, Grant NIDDK R43DK082050. The United States government has certain rights to this invention.

FIELD OF THE INVENTION

The present invention relates generally to methods for the isolation and propagation of cells. More specifically, the invention relates to methods for the isolation and propagation of large numbers of cells for use, for example, in biotherapeutic devices, such as devices for renal replacement therapy, for the treatment of acute renal failure, (ARF), acute tubular necrosis (ATN), multi-organ failure (MOF), sepsis, cardiorenal syndrome (CRS) and end-stage renal disease (ESRD).

BACKGROUND

Acute renal failure and chronic renal disease (CRD) are distinctly different disease processes. The current therapy for both disorders is suboptimal. ARF arises from toxic or ischemic (usually simultaneous) tubule damage from antibiotics, chemo-therapeutic agents, or shock during infectious or major operative procedures. The development of ARF in a hospitalized patient results in a 5 to 8 fold higher risk of death (Chertow et al. (1998), AM. J. MED. 104:343-348; Bates et al. (2001), CLIN. INFECT. DIS. 32:686-693; Humes (1995), KIDNEY INT. 48:S26-S32) with overall mortality rates exceeding 50%. However, if the patient survives the episode of ARF, the regenerative repair processes within the kidney can result in a return of kidney function in 90 to 95% of patients with this acute disorder. Sepsis and cardiorenal syndrome are also acute renal diseases and lead to multiorgan dysfunction.

Sepsis frequently leads to ATN, ARF and MOF with approximately 700,000 cases per year in the United States. The most serious forms of sepsis result in severe sepsis (250,000 annual cases in the U.S.) or septic shock (85,000 annual cases in the U.S.) with mortality rates of greater than 30 and 50 percent, respectively (Schrier et al. (2004), N. ENGL. J. MED. 351(2):159-169).

CRS is defined as a clinical disorder in patients with concomitant cardiac congestive heart failure (CHF) and renal dysfunction in which the therapy to relieve the congestive symptoms of heart failure, usually with diuretics, results and is limited by further declines in renal function. Currently, five million people in the U.S. have cardiac failure, with 350,000 of them having CRS (Shlipak et al. (2004), CIRCULATION 110 (12):1514-1517). Declining renal function in patients with CHF is the most predictive variable for survival rates, not cardiac function (Gottlieb et al. (2002), J. CARD. FAIL. 8(3): 136-141; Fonarow et al. (2005), JAMA 293(5):572-580), thus highly suggestive of a nephrogenic etiology of this syndrome. Current therapies for acute decompensation of heart failure with renal insufficiency are ineffective. In fact, diuretic resistance in CRS results in an increased use of inotropic agents with higher risk of cardiac arrhythmias and ischemia.

Unlike ARF, CRD is an irreversible process of progressive kidney damage commonly from diabetes and hypertension which leads to end-stage renal disease. Patients with ESRD on dialysis continue to have major medical, social and economic problems and a life expectancy of only 4-5 years (Iglehart (1993), N. ENGL. J. MED. 328:366-371; Excerpts from United States Renal Data System: Annual Data Report (1998), AM. J. KIDNEY DIS. 32:S69-S80; Xue et al. (2001), J. AM. SOC. NEPHROL. 12:2753-8; Cukor et al. (2007), J. AM. SOC. NEPHROL. 18:3042-3055). While the standard for kidney replacement therapy for ESRD remains organ transplant, with less than 10,000 kidney transplants completed each year and the current number of patients awaiting transplantation approaching 60,000 (Collins et al. (2005), AM. J. KIDNEY DIS. 45(1 Suppl 1):A5-7), the need far exceeds availability. For all disease processes, available renal replacement therapies consisting of hemofiltration, hemodialysis or chronic ambulatory peritoneal dialysis are non-physiologic and fail to address the homeostatic, regulatory, metabolic, and endocrine functions of the kidney. Patients with ESRD are at high risk for cardiovascular and infectious diseases despite conventional renal replacement therapy. A recent clinical trial failed to show survival benefit from increased doses of dialysis above the current standard of care (Iglehart (1993), N. ENGL. J. MED. 328:366-371), suggesting that there are important metabolic derangements not adequately treated with conventional dialytic treatment. Survival of renal transplant recipients far exceeds that of age-, sex-, and risk-matched controls awaiting transplant, indicating that there is some metabolic function provided by the kidney beyond filtration. Candidate biological markers that are known to be dysregulated in ESRD, correlated with poor outcome and linked to known mechanisms of disease, are markers of inflammation and oxidative stress. ESRD currently effects over 430,000 U.S. patients and has an annual cost of more than 25 billion dollars, and patient numbers are expected to increase to 2.24 million by 2030 (Collins et al. (2005), AM. J. KIDNEY DIS. 45(1 Suppl 1):A5-7). Thus, the development of renal epithelial cell (REC) therapy to replace these functions of the kidney promises to add significant value to the current suboptimal treatments of renal failure.

SUMMARY OF THE INVENTION

Enhancement of cell propagation, such as enhancing kidney cell expansion, can provide the biomass for cell-based therapeutic products for clinical indications of various diseases. It is contemplated that the methods and protocols described herein will lead to improving the quality of, and potentially extend, life for patients with impaired renal function. To this end, the therapeutic potential of a bioartificial renal tubule has been demonstrated with a hollow fiber-based renal assist device (RAD) (Humes et al. (2003), BLOOD PURIF. 21:64-71; Humes et al. (2003), CRIT. CARE MED. 31(10):2421-8). RADs have been constructed using human cells and evaluated in preclinical large animal studies and Phase I/II clinical trails of ARF (Humes et al. (1999), KIDNEY INT. 55:2502-2514; Humes et al. (2002), AM. J. KIDNEY DIS. 39(5):1078-1087; Humes et al. (1999), NAT. BIOTECHNOL. 17:451-455; Fissell et al. (2002), BLOOD PURIF. 20:55-60; Fissell et al. (2003), J. AM. SOC. NEPHROL. 14:454-461). To address the needs of ESRD patients, technology for a wearable bioartificial kidney (WE-BAK) device has been developed to provide continuous physiologic renal support. WEBAK devices differ from the hollow fiber based RAD in that cells are cultured on compact, durable carbon-based disks that are then placed in an extracorporeal ultrafiltrate or peritoneal fluid circuit. Ultrafiltrate or peritoneal fluid provides nutrients and allows cells to respond to the host system. WEBAK devices are designed for durability and are more suitable than RAD to provide long term physiologic support for ESRD. Promising large animal studies are currently in progress using a WEBAK device in an allogenic sheep model. Critical to providing renal replacement therapy for ESRD in the clinical setting will be the efficient construction of WEBAK devices using human REC (HREC). Cells for use in cell-based therapeutic devices, including but not limited to WEBAK devices, can be obtained according to the methods described herein.

In one aspect, the present invention relates to a method for enhanced propagation of cells from a sample. The method includes promoting expansion of precursor cells from the sample, thereby to enhance propagation of a cell population from the sample. This aspect can include one or more of the following features. The sample can be a kidney sample. The precursor cells can be renal precursor cells. During the procedure, the precursor cells can be maintained in an undifferentiated state. The method can increase the number of precursor cells relative to the number present in the sample. The method can include dilution of cells in the sample and/or dilution of cells in a culture or subculture derived from the sample. The enhanced propagation cell population can include renal cells. The method can retain non-adherent cells, for example during changes of growth media during culturing. The method can further include administering retinoic acid.

In another aspect, the present invention relates to a method for enhanced propagation of renal cells from a kidney sample. The method includes (a) treating the kidney sample to produce tissue fragments having a dimension of about 212 µm or less in size; (b) harvesting at least a portion of the tissue fragments by centrifugation at greater than about 50×(g) to produce a pelleted slurry; (c) applying a portion of the pelleted slurry produced in step (b) to a solid support (e.g., a tissue culture plate or other growth surface) and culturing the cells from the pelleted slurry in the absence of retinoic acid and under conditions to permit the renal cells to attach to the solid support and divide; (d) harvesting the cells produced in step (c) prior to reaching confluence on the solid support; (e) applying a portion of the cells harvested in step (d) to a solid support and culturing the cells in the absence of retinoic acid and under conditions to permit the renal cells to attach to the solid support and divide; and (f) harvesting the cells produced in step (e) to produce a propagated population of renal cells. Non adherent cells can be retained when culture growth medium is changed. This aspect of the invention can also have any one or more of the features described above or below.

In another aspect, the method for the enhanced propagation of cells from a sample includes separating the sample into fragments about 212 µm or less in size to produce a slurry; centrifuging the slurry at greater than about 50×(g) to produce a pelleted slurry; creating a culture by applying to a growth surface (e.g., a tissue culture plate or other solid support) about 10 µL or less of the pelleted slurry per square centimeter of surface area of the surface on which the cells in the culture will grow (e.g., a tissue culture plate or other solid support); and subculturing, typically prior to confluence, about $8.7 \times 10^4$ or fewer cells from the culture per square centimeter of surface area on which the subculture is to be grown. In certain embodiments, the method further includes adding retinoic acid after the subculturing step. In certain embodiments, the sample is a kidney sample. In certain embodiments, the non-adherent cells are retained when culture or subculture growth medium is changed. The subculturing step can be repeated with subsequent subcultures such that these further subcultures are initiated by subculturing about $8.7 \times 10^4$ or fewer cells from the previous subculture per square centimeter of surface area on which the further subculture is to be grown. This aspect of the invention can also have any one or more of the features described above or below.

It is to be understood that the features of the various embodiments described herein are not mutually exclusive and may exist in various combinations and permutations. The foregoing aspects and embodiments of the invention may be more fully understood by reference to the following figures, detailed description and claims.

BRIEF DESCRIPTION OF THE DRAWINGS

The invention is illustrated, but is not limited by, the annexed drawings.

FIG. 10 is a table that summarizes the yield calculations from porcine REC propagated using the enhanced propagation method of the invention at 1:16 initial plating density. The actual cell yield from the enhanced propagation method as compared to the historic method is shown. Yield is also translated into cell doublings and the number of devices that can be manufactured using $10^8$ cells per device.

FIG. 16A shows the negative control, and γGT activity is shown in FIG. 16B.

FIG. 24 is a table that summarizes the yield calculations from human REC propagated using the enhanced propagation method of the invention at 1:16 initial plating density. Five human REC samples (A-E) isolated from five individual donors were tested. The actual cell yield from the enhanced propagation method as compared to the historic method is shown. Yield is also translated into cell doublings and the number of devices that can be manufactured using $10^8$ cells per device. A sixth human REC sample (F) was tested in a punch biopsy experiment. In this case, yield calculation through passage four is shown.

DETAILED DESCRIPTION OF THE INVENTION

Figure 1:
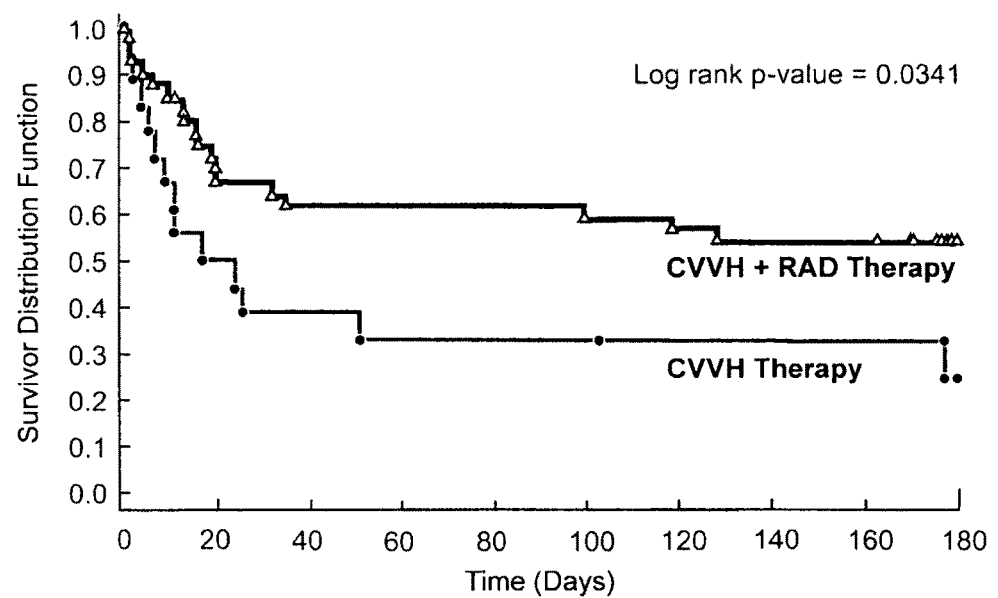
FIG. 1 is a Kaplan-Meier survival curve for critically ill patients receiving RAD therapy over a course of 180 days as compared to the control group receiving no therapy.

Cell therapy, for example, renal cell therapy, promises to improve the survival and overall health of patients suffering from various diseases, including ARF, ATN, MOF, sepsis, CRS, and ESRD. To this end, therapeutic biological devices addressing the physiologic component of cell replacement therapy, such as renal cell replacement therapy, are being developed. Use of this technology in a clinical setting requires manufacture of devices containing available human, or other mammalian, cells. For acute care situations involving cell-based therapeutic devices, it is beneficial to have such devices readily available. As such, these devices typically use xenogenic or allogenic cells in order to have the cells available for rapid use (either to add to a device as needed or to pre-populate a device during manufacturing). For example, as described in Examples 1 and 2, methods according to the invention can be used to provide such cells. However, for chronic care situations, autogenic cells (in addition to xenogenic or allogenic cells) may be used to populate cell-based therapeutic devices. For example, as described in Example 3, tissue from a kidney biopsy can be used according to the methods of the invention to provide cells to populate such devices. Thus, a patient's own cells can be sampled, grown, and used in a cell-based therapeutic device used to treat that patient.

The overall goal of the present invention is to employ cell propagation protocols which result in the isolation and propagation of more human cells, such as renal epithelial cells, than was possible with historic methods. Specifically, the enhanced propagation methods of the present invention seek to promote the expansion of precursor cells to increase cell yield in the resulting cell population. For example, the methods described herein apply conditions that stimulate and/or amplify precursor cells, thus increasing the number of precursor cells in a sample. In some embodiments, the methods involve one or more of (1) more efficient enzymatic digestion of a sample tissue, (2) use of smaller tissue particle sizes (e.g., about 212 μm or less), (3) the use of higher centrifugal forces on a digested tissue sample to generate a pelleted slurry that includes more precursor cells, (4) dilution of cell density (e.g., dilution during initial plating (plating density) and/or dilution during subculturing (passage ratio)), and (5) maintaining passaged cells at subconfluent conditions during expansion. The methods also can involve partial media changes and techniques to retain non-adherent cells to promote a proliferative environment for precursor cells. Retinoic acid to induce terminal differentiation can be added to cell cultures produced from enhanced propagation methods of the invention (i.e., enhanced propagation cell cultures) just prior to their use to maintain the precursor cells in an undifferentiated state. The retinoic acid, or other differentiation factor, can be absent from culturing and/or subculturing steps. It is contemplated that any one, or any combination of two or more, of these condition variables may be employed to enhance cell propagation.

In certain embodiments, a tissue sample, such as a kidney tissue sample, is separated into suitable fragments (e.g., by enzymatically digesting the sample and/or by sieving a fragmented sample into fragments about 212 μm or less in size) to generate a slurry. The slurry is centrifuged (e.g., at greater than about 50×(g)) to generate pelleted slurry. Typically, pelleted slurry is a cell suspension in which the cells are more concentrated than the original slurry (centrifugation that produces the pelleted slurry can be followed by removal of supernatant). The resulting pelleted slurry is plated (or otherwise provided to a growth surface) to generate a culture. For example, about 10 μL or less of the pelleted slurry is applied per square centimeter of surface area of the tissue culture plate on which the culture is to be grown (or other surface on which the cells in the culture will grow). Cells from the culture, typically prior to confluence, are then subcultured (e.g., using about $8.7 \times 10^4$ or fewer cells from the culture per square centimeter of surface area on which the subculture is to be grown). This subculturing step can be repeated by subculturing, typically prior to confluence, the previous subculture (e.g., using about $8.7 \times 10^4$ or fewer cells from the previous subculture per square centimeter of surface area on which the further subculture is to be grown). Any of these steps can be done in the absence of a differentiating factor (e.g., retinoic acid).

The enhanced propagation methods and resulting cell populations are beneficial in the cell therapy field. Accordingly, methods according to the present invention combined retention of therapeutic potential with manufacturing feasibility for human REC. Cell yield per human donor kidney is contemplated to meet projected clinical need. Certain embodiments of the present invention encompass optimizing human REC integration into bioartificial renal epithelial cell-based devices currently being developed using animal cells, followed by evaluation of efficacy using pre-clinical large animal models of chronic renal failure, ARF and sepsis.

It is contemplated that the methods described herein are applicable to a variety of cells, including various renal cells. For example, in instances where cells are harvested from organs (either from living donors having given proper consent or from cadavers whose tissues were properly donated), it is contemplated that cells can be expanded according to the methods described herein. It should also be understood that it is contemplated that the methods described herein are applicable at least to mammalian, including human, cells.

Stem Cells and REC Progenitors

A methodology to isolate and grow REC from adult human kidneys has been published (Smith et al. (2006), METHODS ENZYMOL. 419:194-207). The described methods were used to provide the renal cell component of RADs for large animal and clinical studies. However, using current cell processing techniques, REC isolated from human transplant discards have the projected expansion capability to meet the need for short term ARF but not that for continuous ESRD therapy. As of 2002, there were over 430,000 ESRD patients in the U.S. and this number is projected to increase to 2.3 million by 2030 (Collins et al. (2005), AM. J. KIDNEY DIS. 45(1 Suppl 1):A5-7). Clinical and experimental observations suggest that REC progenitor cells have immense proliferative potential as evidenced by complete tubule regeneration to reform a fully functional and differentiated epithelium after severe nephrotoxic or ischemic injury. The role of stem cells in tubule regeneration is still being explored. It is theoretically possible to guide the differentiation of totipotent embryonic stem cells down an intricately orchestrated renal path.

Unfortunately, this technology is still in its infancy and does not provide a timely solution to cell sourcing for renal replacement therapy. Researchers have gone to great lengths to ascribe this regeneration potential to hematopoetic or mesenchymal adult stem cells with controversial results (Kale et al. (2003), J. CLIN. INVEST. 112:42-49; Poulsom et al. (2001), J. PATHOL. 195:229-235; Herrera et al. (2004), INT. J. MOL. MED. 14(6):1035-41; Gupta et al. (2002), KIDNEY INT. 62(4):1285-90). The most pertinent observation from these studies was that injection of mesenchymal stem cells post ischemic injury enhances the regenerative potential and recovery of tubules, occurring without actual incorporation of these cells into the regenerated tubules, possibly due to an endocrine effect (Bi et al. (2007), J. AM. SOC. NEPHROL. 18(9):2486-96; Iwatani et al. (2007), J. AM. SOC. NEPHROL. 18:2423-2428). Current opinion is that precursors responsible for the repopulation of tubules reside within the kidney, though the defining characteristics and mechanism are still under exploration (Duffield et al. (2005), KIDNEY INT. 68(5):1956-61; Challen et al. (2006), J. AM. SOC. NEPHROL. 17(7):1896-912; Al-Awqati et al. (2006), STEM CELL REV. 2(3):181-4). Regardless of source, these resident kidney progenitor cells have stem cell-like characteristics with a high capacity for self-renewal and the ability to differentiate under defined conditions into mature somatic cells as evidenced by tubule regeneration (Hall et al. (1989), DEVELOPMENT 106:619-633; Potten et al. (1990), DEVELOPMENT 110:1001-1020). Accordingly, methods of the invention that are improvements over the historic isolation methodology and more closely mimic the in vivo environment, enhance REC propagation potential.

Isolation and Amplification of REC Progenitors

Human REC populations are derived from human kidney transplant discards found unsuitable for transplantation due to anatomic or fibrotic defects. Thus, the number of available kidneys is limited and tissues are suboptimal, usually from older donors with indices that preclude kidneys from being suitable for donation. Additionally, organs undergo 24 to 36 hours of cold ischemia (average time range from organ procurement to REC isolation), causing damage to differentiated tubules much like acute tubular necrosis (ATN). Historic REC isolation proceeds as follows: the kidney cortex is removed and mildly digested, slurry is passed through a 600 μm sieve and plated densely onto collagen IV (COLIV) coated/fetal calf serum (FCS) adsorbed dishes. After 24 hours, all non-adherent tissue is removed, and the differentiating factor retinoic acid (RA) is included in the culture media after initial confluence is achieved. By focusing on the isolation of whole tubules and the maintenance of REC in fully differentiated epithelial sheets, this method greatly sacrifices the proliferation potential of isolated cells.

Figure 3:
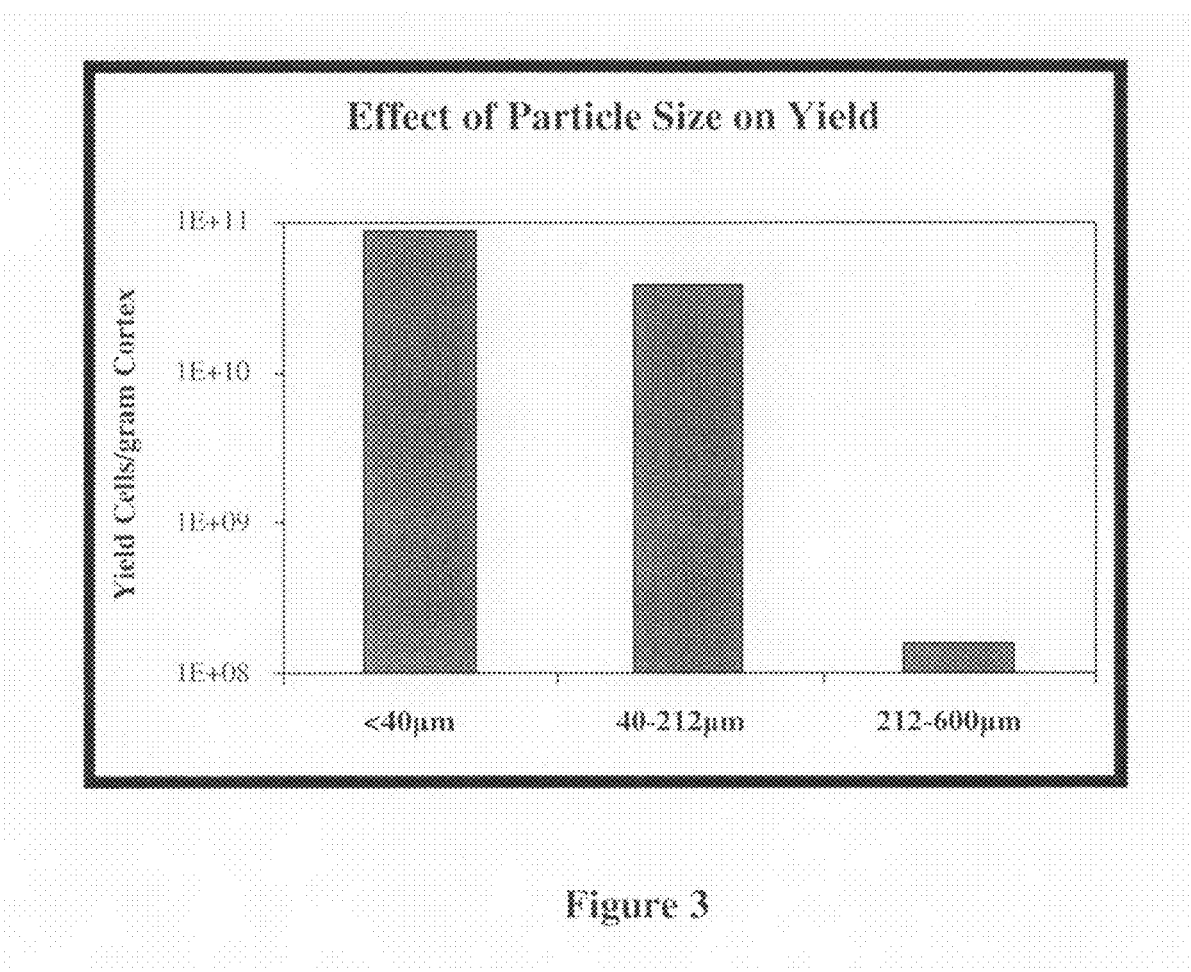
FIG. 3 is a histogram showing the effect of particle size on cell yield for porcine REC. Yield through one month is shown.

Therefore, methods according to the invention promote precursor expansion to increase REC yield. In certain embodiments, primitive kidney progenitors are amplified to produce a large biomass without contact inhibition, with retinoic acid being added to induce functional differentiation just prior to use. With the historic isolation method, mild digestion and low centrifugal force during washes leads to the isolation of only the healthiest, intact tubules while more buoyant, damaged tubules having high proliferative potential are removed in the supernatant. In accordance with the invention, more complete digestion of cortex tissue disrupts tubule basement membranes and stimulates repopulation, as seen in ATN. For example, as shown in FIG. 3, more efficient digestion of the porcine cortex slurry to fragments of about 212 μm or smaller enhanced cell yield by almost three orders of magnitude. It is contemplated that use of tissue fragments of about 212 μm or smaller, of about 200 μm or smaller, of about 150 μm or smaller, of about 100 μm or smaller, of about 50 μm, of about 40 μm or smaller, of about 30 μm or smaller, of about 20 μm or smaller, and of about 10 μm or smaller can enhance cell yield. Additionally, higher centrifugal force washes to generate a pelleted slurry, in accordance with the invention, results in a more inclusive population of cells, likely retaining all regenerating cells as well as those that contribute mechanistically by the secretion of endocrine factors. For example, it is contemplated that centrifugation during washes at greater than about $50 \times (g)$, greater than about 100×(g), greater than about 150×(g), greater than about 200× (g), greater than about 250×(g), and greater than about 300× (g) can be applied. For example 300×(g) can be used to generate a pelleted slurry. Typically, a centrifugation wash is conducted for about five minutes. Additionally, specific gravity lower than 50×(g) can be used if the time of centrifugation is increased. The notation "×(g)" refers to "times gravity" such that, for example, 300×(g) means 300 times gravity.

Figure 2:
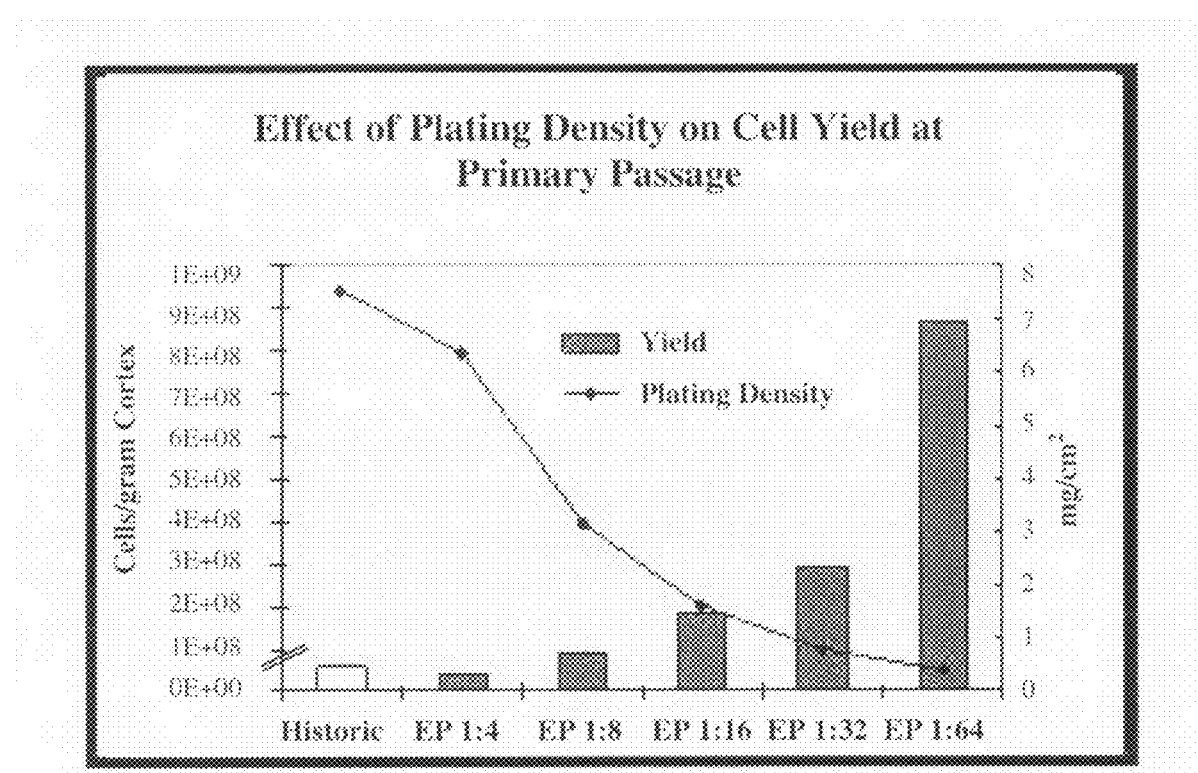
FIG. 2 is a histogram showing the effect of plating density on cell yield at primary passage for porcine REC.

Dilute plating density and passage ratio to avoid contact inhibition, partial media changes and retention of non-adherent cell populations according to the invention contribute to the prolonged maintenance of the proliferative environment. As shown in FIG. 2, plating density significantly impacts cell yield. Methods according to the invention contemplate initial plating of the pelleted slurry at about 10 μL or less of pelleted slurry/cm² tissue culture plate, where 1 gram of porcine cortex yields about 340 μL of pelleted slurry and 1 gram of human cortex yields about 167 μL of pelleted slurry. The amount of pelleted slurry to be used is based upon pelleted slurry obtained from tissue, such as kidney tissue, that is digested and separated into tissue fragments of about 212 μm or smaller and is washed using centrifugation at greater than about 50×(g). It is contemplated that initial plating (or provision to another cell growth surface) of the pelleted slurry can occur at about 10 μL or less of pelleted slurry/cm² tissue culture plate (or other cell growth surface), about 8 μL or less of pelleted slurry/cm² tissue culture plate (or other cell growth surface), about 5 μL or less of pelleted slurry/cm² tissue culture plate (or other cell growth surface), about 3 μL or less of pelleted slurry/cm² tissue culture plate (or other cell growth surface), about 2 μL or less of pelleted slurry/cm² tissue culture plate (or other cell growth surface), about 1 μL or less of pelleted slurry/cm² tissue culture plate (or other cell growth surface), about 0.5 μL or less of pelleted slurry/cm² tissue culture plate (or other cell growth surface), about 0.1 μL or less of pelleted slurry/cm² tissue culture plate (or other cell growth surface), or about 0.05 μL or less of pelleted slurry/cm² tissue culture plate (or other cell growth surface). Any of the plating densities shown in Table A can be used as well. Because the plating density concept can be expressed in several ways, Table A shows the correspondence between each method of expression. Briefly, experiments were conducted using the plating density of the historical method as a baseline. Thus, the experimental plating density conditions of the enhanced propagation techniques are typically expressed as a fraction of the historical plating density. These fractions correspond to numerical volumes of pelleted slurry, as shown in Table A. It should be understood that while plating on tissue culture plates is discussed, the plating densities described herein are relevant to any culture method where cells are grown on a surface. Thus, any growth surface, such as culture flasks and the like, are equally applicable to the concepts described herein.

TABLE A

Initial Plating Density According to Enhanced Propagation Methods of the Invention.

| Initial Plating Density Ratio (Tissue amount used in Enhanced Propagation Method:Tissue amount used in Historical Method) | Amount of Pelleted Slurry Per 100 mm Tissue Culture Plate | Amount of Pelleted Slurry Per Square Centimeter of Surface Area on Which Cells Will Grow* |
|---|---|---|
| 1:4 | 128 μl | 2.22 μl |
| 1:8 | 64 μl | 1.11 μl |
| 1:16 | 32 μl | 0.55 μl |
| 1:32 | 16 μl | 0.28 μl |
| 1:64 | 8 μl | 0.14 μl |
| 1:128 | 4 μl | 0.07 μl |

*Calculation is based on the surface area of a 100 mm plate, which equals 57.7 cm². The calculation is (Amount of Pelleted Slurry Per 100 mm Tissue Culture Plate)/57.7 cm². Thus, this table can be expanded for other plating densities using this table, and the associated calculations, as a template.

Optionally, the pelleted slurry can be resuspended before plating (or provision to another cell growth surface). If resuspended, the amount of pelleted slurry is adjusted mathematically. For example, if 1 mL total of pelleted slurry is created by the digesting, separating, and washing steps, and it is resuspended in 1 mL of fluid, then 20 μL or less of the resuspended pelleted slurry/cm² tissue culture plate is used. If 1 mL total of pelleted slurry is created by the digesting, separating, and washing steps, and it is resuspended in 9 mL of fluid, then 100 μL or less of the resuspended pelleted slurry/cm² tissue culture plate is used.

Subculturing is accomplished by passaging the culture (or subsequent subcultures), typically prior to confluence (confluence is about $1.7 \times 10^5$ cells/cm² for human RECs), using about $8.7 \times 10^4$ or fewer cells from the culture per square centimeter of surface area on which the subculture is to be grown. This subculture dilution ratio is also referred to herein as passage ratio. It is contemplated that any number of cells from about $8.7 \times 10^4$ or lower can be used. For example, about $8.7 \times 10^4$ or fewer cells can be used, about $8.0 \times 10^4$ or fewer cells can be used, about $7.0 \times 10^4$ or fewer cells can be used, about $6.0 \times 10^4$ or fewer cells can be used, about $5.0 \times 10^4$ or fewer cells can be used, about $4.0 \times 10^4$ or fewer cells can be used, about $3.0 \times 10^4$ or fewer cells can be used, about $2.0 \times 10^4$ or fewer cells can be used about $1.0 \times 10^4$ or fewer cells can be used, about $5.0 \times 10^3$ or fewer cells can be used, about $2.0 \times 10^3$ or fewer cells can be used, and about $1.0 \times 10^3$ or fewer cells can be used can be used. Any of the subculturing ratios shown in Table B can be used as well. Because the passage ratio concept can be expressed in several ways, Table B shows the correspondence between each method of expression. The values in the columns of Table B are calculated as follows. It is estimated, based upon empirical studies, that the number of human renal cells on a confluent 100 mm plate having a surface area of 57.7 cm² is $10^7$. This number is divided by the dilution factor (e.g., a passage ratio of 1:16 has a dilution factor of 16) to yield the Number of cells to be plated per 100 mm tissue culture plate. The result is the number in the second column of Table B. Then, the value in the second column is divided by 57.7 cm² to yield the number of cells to be plated per square centimeter of the surface area on which the cells will grow. Knowing this number, even though a culture or subculture may not be confluent, one can determine how much to "dilute" the growing cells on each passage by knowing how many cells to add to the new culture surface. Furthermore, because different cell types may have slightly different cell numbers on a 100 mm tissue culture plate at confluence, the absolute number of cells to be provided for a particular passage ratio may vary slightly. However, once the number of cells at confluence is known, the absolute number of cells to be provided (and, hence, the passage ratio) can be calculated for any cell type. It should also be understood that while plating on tissue culture plates is mainly discussed herein, the passage ratios described herein are relevant to any mode of subculturing where cells grow on a surface. Thus, any growth surface, such as culture flasks and the like, are equally applicable to the concepts described herein.

TABLE B

Subculturing Ratio

| Passage Ratio | Number of Cells Plated Per 100 mm Tissue Culture Plate | Number of Cells Plated Per Square Centimeter of Surface Area on Which Cells Will Grow* |
|---|---|---|
| 1:2  | $50.00 \times 10^5$ | $8.7 \times 10^4$ |
| 1:4  | $25.00 \times 10^5$ | $4.3 \times 10^4$ |
| 1:8  | $12.50 \times 10^5$ | $2.2 \times 10^4$ |
| 1:16 | $6.25 \times 10^5$  | $1.1 \times 10^4$ |
| 1:32 | $3.13 \times 10^5$  | $5.4 \times 10^3$ |
| 1:64 | $1.56 \times 10^5$  | $2.7 \times 10^3$ |

*Calculation is based on the surface area of a 100 mm plate, which equals 57.7 cm$^2$.

Historically, RA was used to promote tubule cell differentiation, but since it also reduces the doubling potential of REC precursors, methods according to the invention typically remove RA from cultures and/or subcultures until terminal differentiation just prior to use.

Application of these concepts to porcine REC isolation resulted in greater than a $9.6 \times 10^6$ fold increase in cell mass prior to final senescence. During the expansion phase there was no indication of advanced senescence of the propagating cells or detected decrease in REC purity or therapeutic potential. This increase in biomass can be thought of in terms of the number of devices (e.g., the RAD device) to be manufactured from a kidney isolate. Historical manufacturing practices yield 5-10 devices per donor kidney, with the maximum production of 100,000 RAD annually. In contrast, methods according to the invention for enhanced cell propagation are contemplated to increase manufacturing potential by at least four orders of magnitude, allowing for the construction of 100,000 units per donor kidney or 1,000,000,000 devices annually.

Clinical Evaluation of Efficacy of Renal Cell Therapy

After encouraging pre-clinical animal data, including the use of a porcine SIRS model, the FDA approved a Phase I/II clinical trial to evaluate the safety and efficacy of renal cell therapy utilizing the RAD on ten critically ill patients with ARF and multiorgan failure receiving continuous venovenous hemofiltration (CVVH). The predicted hospital mortality rates for these patients averaged greater than 85%. The devices were seeded with human renal proximal tubule cells isolated from kidneys donated for cadaveric transplantation but found to be unsuitable for transplantation due to anatomic or fibrotic defects. The results of this clinical trial demonstrated that the experimental treatment could be delivered safely under study protocol guidelines for up to 24 hours when used in conjunction with CVVH. The clinical data indicated that the RAD exhibited and maintained viability, durability, and functionality in this clinical setting. Cardiovascular stability of the patients was maintained, and increased native kidney function, as determined by elevated urine outputs, temporally correlated with RAD treatment. The device also demonstrated differentiated metabolic and endocrinologic activity. All but one treated patient with more than a three day follow-up showed improvement, as assessed by acute physiologic scores. Six of the ten treated patients survived past 28 days with kidney function recovery, although mortality rates predicted for these ten patients using the acute physiology, age, chronic health evaluation (APACHE) 3 scoring system were on average 85 percent. Plasma cytokine levels suggest that RAD therapy produces dynamic and individualized responses in patients depending on their unique pathophysiologic conditions.

These favorable Phase I/II trial results led to a subsequent FDA-approved, randomized, controlled, Phase II investigation at 12 clinical sites to determine whether this cell therapy approach alters patient mortality. This Phase II study involved 58 patients, of whom 40 were randomized to RAD therapy and 18 made up a control group with comparable demographics and severity of illness by SOFA scores. The incidence of sepsis in this clinical trial was 73% in the RAD treated group and 67% in the control group. The efficacy of the RAD in patients with sepsis demonstrates the ability of renal cell therapy to reverse sepsis in the clinical setting. The early results were as compelling as the Phase I/II results. Renal cell therapy improved the 28-day mortality rate from 61% in the conventional hemofiltration-treated control group to 34% in the RAD-treated group (Tumlin et al. (2008), J. AM. SOC. NEPHROL. 19(5):1034-40). This survival impact continued through the 90- and 180-day follow-up periods (p<0.04), with the Cox proportional hazard ratio indicating that the risk of death was 50% of that observed in the conventional CVVH group (FIG. 1).

Of note, the RAD clinical trial was halted due in part to manufacturing hurdles that could not be overcome due to resource limitations. These manufacturing difficulties were caused predominantly by the need to maintain the RAD in culture prior to clinical use, demanding significant hands-on technical time. The WEBAK device design allows for the device to be both miniaturized and cryopreserved, mitigating some of the shortcomings of the RAD design.

The invention will now be illustrated by means of the following examples which are given for the purpose of illustration only and without any intention to limit the scope of the present invention.

EXAMPLES

Example 1

A pilot study was initiated using a porcine kidney to determine which variables have an effect on REC propagation. The variables tested included enzymatic digestion, particle size, centrifugation, plating density and media changes, plating matrix, subculture conditions, and the use of differentiation factors. In accordance with the invention, more efficient digestion of cortex tissue generated slurry that included precursor cells with enhanced proliferative potential. The slurry was further separated by size, and higher centrifugal force was applied to better retain precursor cells. Other variables such as diluting plating density, partial media changes, subculture conditions (e.g., passage ratio), and the retention of non-adherent cells contributed to the prolonged maintenance of a proliferative environment. It is contemplated that any one, or any combination of two or more, of these variables can be used to improve cell yield in accordance to the invention.

(1) Methods

A 22-pound Hampshire mix pig was anesthetized and intubated with isoflurane. Kidneys were perfused with ice cold saline prior to removal from the animal and the isolation proceeded within one hour of removal. Kidneys were dissected and cortex minced at which time the tissue was split into two equivalent groups and further processed using either the historic method or enhanced propagation (EP) protocol of the invention. A complete description of protocol modifications can be found in Table 1, below. It should be understood that the EP protocol shown in Table 1 is one embodiment of the invention. As shown in the experiments below, variations of the conditions shown in Table 1 also are useful to enhance cell yield.

TABLE 1

Comparison of Historic vs. Enhanced Propagation (EP) Protocol

| Step | Historical Method | Enhanced Propagation |
|---|---|---|
| Enzymatic Digestion of Tissue Sample | Use of Collagenase to generate aggregates of less than 600 μm in particle size. | Use of Liberase Blendzyme (available from Roche Applied Science) to generate single cell aggregates of about 150 μm in particle size. Equivalent enzymes can be used. |
| Centrifugation of Tissue Slurry | Centrifugation at 50 × (g) (results in exclusion of single cells and aggregates that may contain damaged and more buoyant tubules). | Centrifugation at 300 × (g) (results in inclusion of single cells and aggregates that may contain damaged and more buoyant tubules). |
| Initial Plating Density | 500 μL pelleted slurry/100 mm plate | 4-32 μL pelleted slurry/100 mm plate, where 32 μL/100 mm plate is a plating density of about 1:16 relative to the historical method. |
| Media Change During Cell Propagation | Media is changed at 24 hours post plating, and non-adherent cells are removed by aspiration. | Media is changed at 7 days post plating and non-adherent cells are retained. |
| Matrix | Collagen IV/adsorbed FCS | No Matrix |
| Sub-Culture to Achieve Plating Dilution | About $10^7$ cells are seeded, and $2 \times 10^7$ cells are recovered at passages 1-4. Passage ratio is 1:2. (100 mm plates are used) | About $6.25 \times 10^5$ cells are plated, and $10^7$ cells are recovered. Passage ratio is about 1:16. (100 mm plates are used) |
| Addition of Differentiation Factor (e.g. RA) | RA is added prior to primary passage. Cells remain differentiated through passages. | RA is added on device or test well just prior to use to signal the end of precursor amplification. Cells remain undifferentiated until immediately prior to use. |

Briefly, for enhanced propagation, changes included using an optimized enzyme blend (Liberase vs. crude collagenase) and raising centrifugation speed to be inclusive of single cells and damaged (more buoyant) tubules. To determine the effect of particle size on yield, the part of the slurry was sieved into three sub-groups, 212-600 μm, 40-212 μm, and less than 40 μm (single cell). To evaluate plating density, cells were serially diluted by a factor of 2 (1:4, 1:8, 1:16, 1:32, 1:64). To allow the maximum time for progenitor migration onto the plate and avoid the removal of autoregulators that are secreted by cells during this initial outgrowth phase, partial media changes were performed as needed and all non-adherent cells (NAC) retained. To determine whether NAC should continue to be included in REC cultures, NAC from 1:16 at first passage were retained as a separate population and tested for REC characteristics. Cultures were further split by passage ratios of 1:8, 1:16, and 1:32, corresponding to 2,500,000, 1,250,000 and 625,000 cells/20 mL/75 cm² flask, respectively. For comparison, all yields are calculated as cells per gram kidney cortex.

(2) Cell Yield Comparison

Plating Density:

As shown in FIG. 2, plating density had a profound and immediate effect on cell yield. There was an inverse relationship between plating density and yield. EP cultures with initial dilutions down to 1:32 were more than 75% confluent after only five days in culture; EP culture with 1:64 dilutions were passaged after seven days; while historic cultures took over 1 week to reach confluence. Therefore, the increased cell yield was not due to longer culture times. Without being bound by theory, it may be that the doubling rate increases in a set pool of precursor cells and/or that the increased dilution stimulates more precursors to enter into a state of transient replication.

Enzymatic Digestion:

A Liberase Blendzyme was used. Liberase Blendzymes are mixtures of highly purified collagenase and neutral protease enzymes, formulated for efficient, gentle, and reproducible dissociation of tissue from a wide variety of sources. The purified collagenase enzymes are isoforms I and II, as specified by the nomenclature of Bond and Van Wart. The target substrates for these enzyme blends are the collagen and non-collagen proteins that comprise the intercellular matrix. As shown in FIG. 3, more efficient digestion of the cortex slurry to fragments smaller than 212 μm had a positive impact on cell yield. Destruction of the tubule structure to less than 40 μm, which would effectively destroy the theoretical, three-dimensional stem cell niche, actually yielded a higher cell number. Cell yield from the larger fragments, obtained from on top of the sieve after the first 20 minutes of enzyme digestion, was almost three orders of magnitude lower than the other fractions tested (note the logarithmic scale of FIG. 3). Possible explanations for the failure to propagate could be increased ischemic death in the more central regions, mechanical barriers to precursor migration or lack of stimulatory factors.

Figure 4:
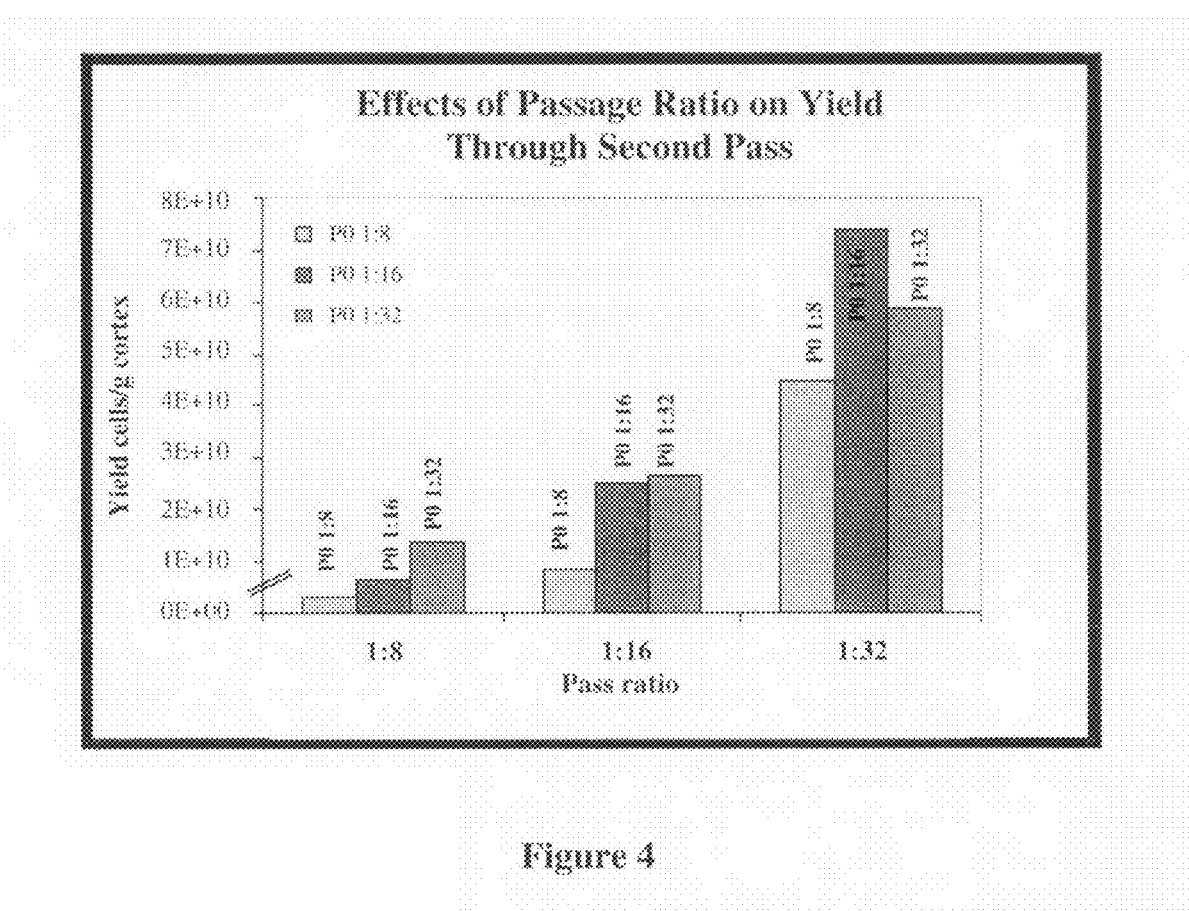
FIG. 4 is a histogram showing the effect of passage ratio on cell yield through second pass for porcine REC.

Sub-Culture:

FIG. 4 shows the effects of passage ratio on cell number. The experiment tested each of EP cultures having initial plating densities of 1:8, 1:16, and 1:32 at passage ratios of 1:8, 1:16, and 1:32. The results show that increased passage ratio improved cell yield. Furthermore, unlike the initial plating, increasing dilution increased the amount of time between passages. Passage was required for 1:8 and 1:16 in 17 days and 1:32 in 28 days. This observation is significant in the context of manufacturing in that equivalent results can be accomplished with less manipulation.

Figure 5:
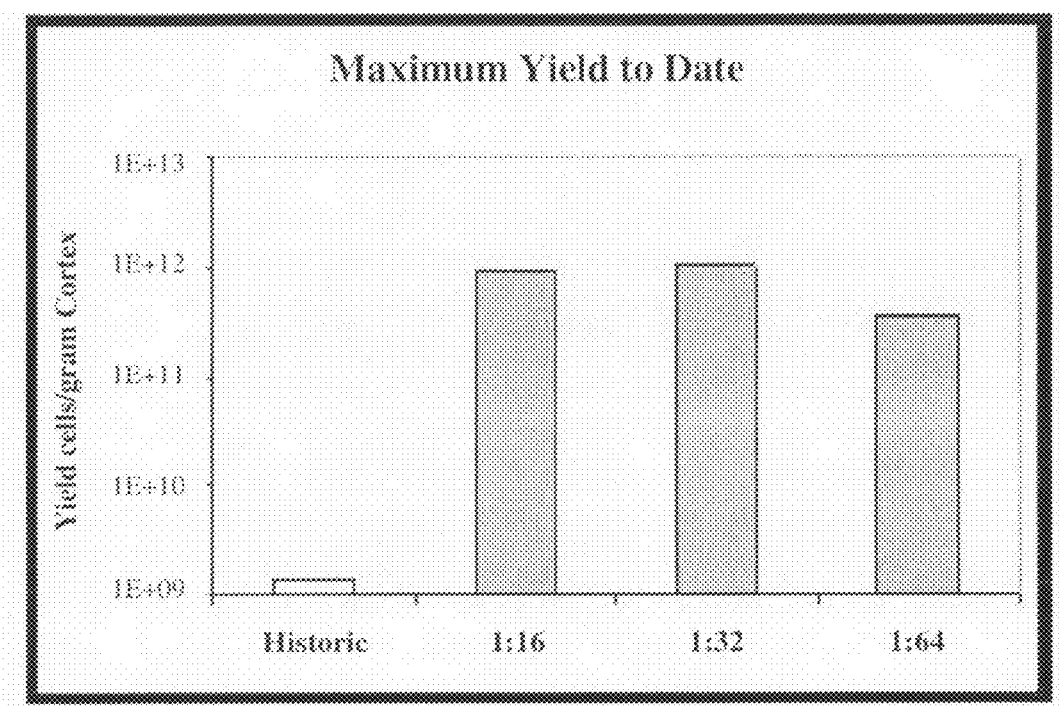
FIG. 5 is a histogram showing the actual cell yield from porcine REC propagated by the enhanced propagation method of the invention compared to the historic cell propagation method.

Cell Yield:

Finally, the actual cell yield from EP method of the invention compared to the historic method is shown in FIG. 5. As shown in FIG. 5, each group had both a plating density and a passage ratio of either 1:16, 1:32, or 1:64. In less than 6 weeks of culture, an equivalent of one trillion cells were propagated from one gram of porcine kidney cortex using the enhanced propagation protocol. In this short time, REC yield was increased 732 fold over that obtained using historic techniques (FIG. 5; Note the logarithmic scale). FIG. 10 shows another REC culture (culture G) using the same method as that described in Table 1 showing a 9,640,288 fold increase in yield. This increase translated into an increase of more than 23 cell doublings.

(3) Morphology

Figure 6:
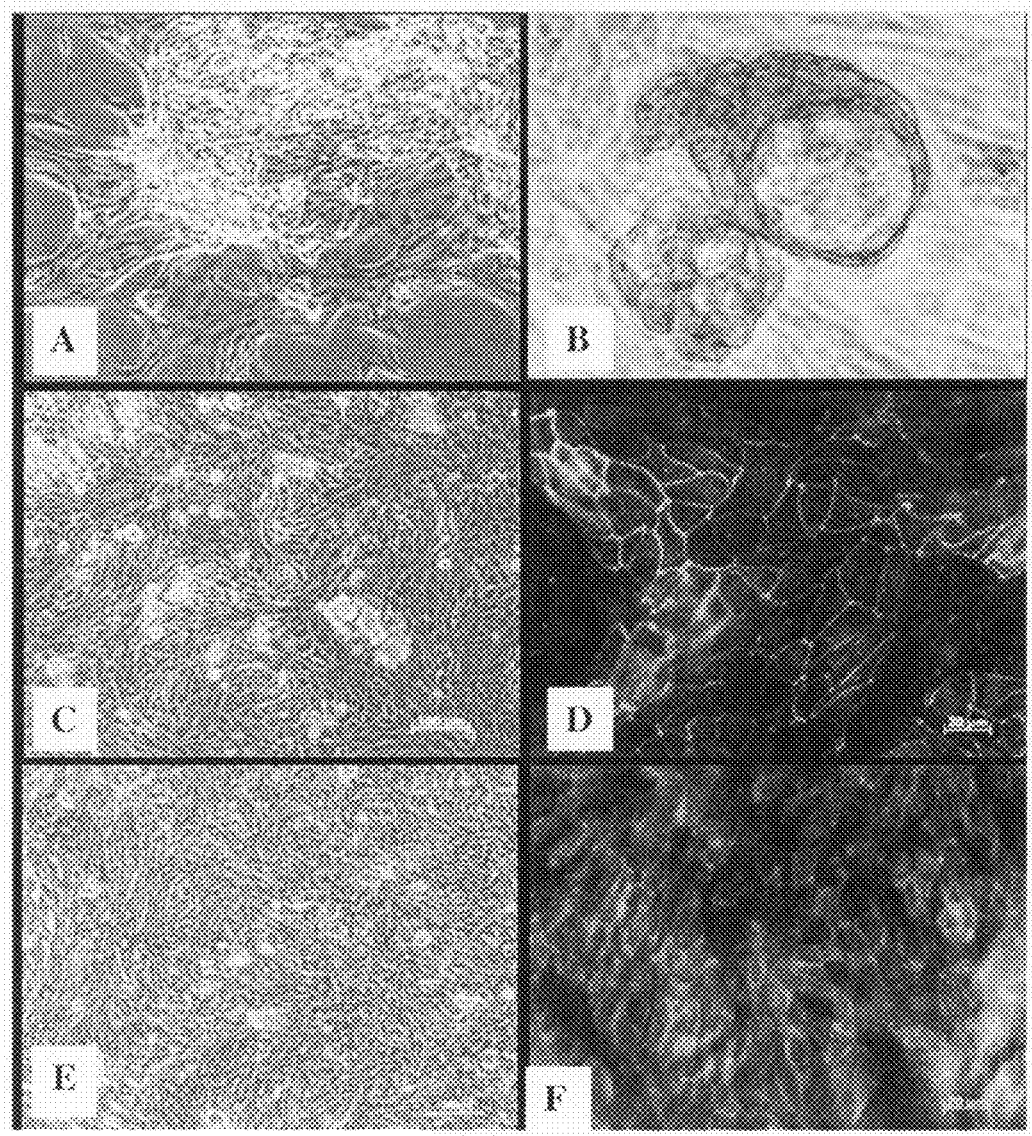
FIGS. 6A-F are photographs showing the morphology of REC propagated using the enhanced propagation method of the invention compared to the historic cell propagation method. The photographs of FIGS. 6A, 6C, and 6E were taken with a 10× objective, and the photographs of FIGS. 6B, 6D, and 6F were taken with a 40× objective.

Cell populations obtained from the more aggressively digested enhanced propagation protocol existed as both an adherent and a non-adherent fraction that either aggregated or expanded to form hollow spheroids (FIGS. 6A and 6B). Spheroids have previously been observed with aggressively digested human kidney tissue, however characterization and proliferation potential was not pursued. Transferring the NAC population to a new flask resulted in a mostly adherent population after two transfers at which point they behaved identically to their adherent counterparts. At higher passage dilutions, EP cells grew in colonies with neoplastic spindle shaped cells migrating from the edge that then obtained the typical cobblestone morphology at the colony center (FIG. 6A). Cell populations obtained from historic protocols existed as tightly packed monolayers with no NAC population after aspiration of supernatant 24 hours post plating. Passage of EP cells at a confluent density ($10^6$ cells/mL/5 cm$^2$) resulted in the formation of a monolayer with typical cobblestone morphology within one day. Even though EP cells were significantly larger, indicating senescence, cultures continued to double. ZO-1 positive tight junctions and punctuate AT-1 positive central cilia indicative of polarized epithelium were evident in all cultures tested. FIG. 6B shows spheroid of non-adherent cells. FIGS. 6C-D and 6E-F are representative of EP populations and historic populations of REC, respectively.

(4) Tubule Differentiation

Figure 7:
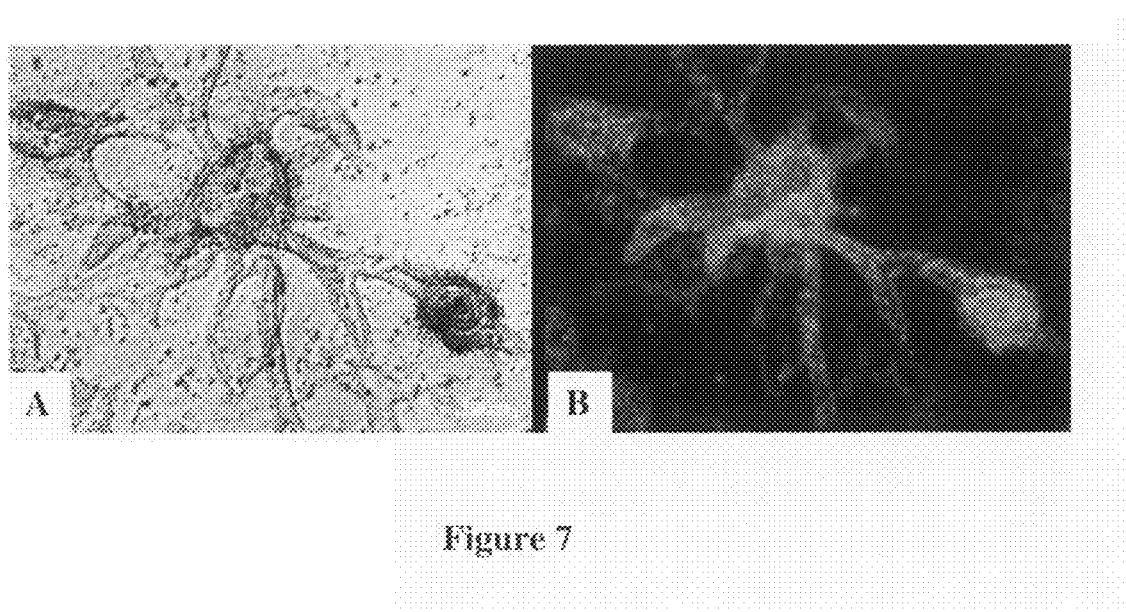
FIGS. 7A and 7B are photographs showing the tubulogenesis potential of porcine REC propagated using the enhanced propagation method of the invention. Tubulogenesis potential was retained in these cells. The photograph of FIG. 7A is a phase-contrast photograph. The photograph of FIG. 7B is tissue stained with DAPI nuclear staining and shows multicellular extensions into the 3D matrix.

The ability to form differentiated tubule structure remains the fundamental characteristic of RECs. After one month of culture, representative EP cell populations were suspended at $10^6$ cells/mL in a three dimensional matrix consisting of Collagens I and IV. Tubulogenesis was stimulated by the addition of 25 ng/mL hepatocyte growth factor (Williams et al. (2003), J. ANAT. 203:483-503; Karihaloo et al. (2005), NEPHRON EXP. NEPHROL. 100:e40 e45), both with and without $10^{-7}$M retinoic acid. After one week, cultures were fixed in 4% paraformaldehyde, permeated with Triton X-100 and nuclei stained with 2-(4-amidinophenyl)-6-indolecarbamidine dihydrochloride (DAPI). Tubulogenesis was observed in all wells tested, including –RA wells (Humes et al. (1992), EXP. CELL RES. 201:8-15). EP cells shown in FIGS. 7A and 7B were originally plated at 1:32 dilution and passaged twice at 1:32. This population had the highest yield comparison of 732 times the historic method.

Figure 8:
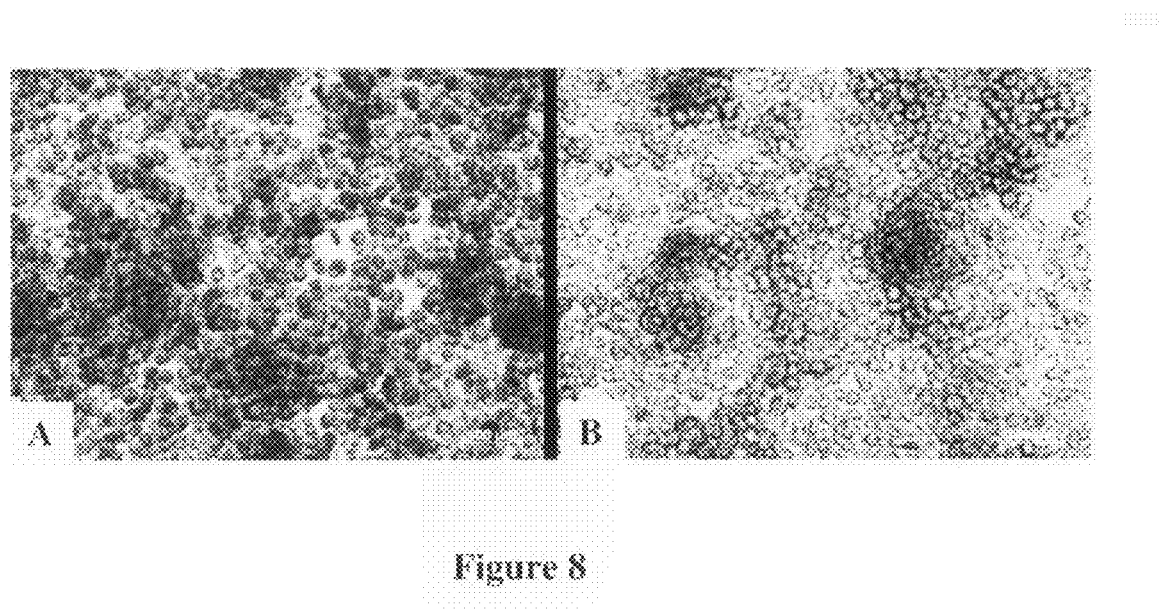
FIGS. 8A and 8B are photographs showing the γGT activity of porcine REC propagated using the enhanced propagation method of the invention with or without the addition of GlyGly, respectively. Activity was detected in the most advanced enhanced propagation cell populations from an initial 1:32 plating density and 1:32 passage ratio after three passages (732 times the yield with the historic method).

(5) Oxidative Stress Response:

γ-glutamyltranspeptidase (γGT) is typically expressed on the apical brush border membrane of proximal tubules and catalyzes the recovery of glutathione. Glutathione deficiency has long been associated with oxidative stress (Curthoys (1983), MINER. ELECTROLYTE METAB. 9:236-245; Wu et al. (2004), J. NUTR. 134(3):489-92). To verify that advanced EP cell populations retained the therapeutic potential to ameliorate oxidative stress, retention of γGT activity was verified using the substrate γ-glutamyl-4-methoxy-2-napthylamide (GMNA), which in the presence of GlyGly and fast blue salt will form an insoluble red pigment (Rutenberg et al. (1968), J. HISTO. CYTO. 17(8):517-526). Activity was detected in the most advanced EP cell population, representing 732 times the historic yield, and was typical of all cultures tested including historic controls (FIG. 8A). Non-specific reactivity as indicated by the no GlyGly control is included as a reference (FIG. 8B).

(6) Cytokine Response

Figure 9:
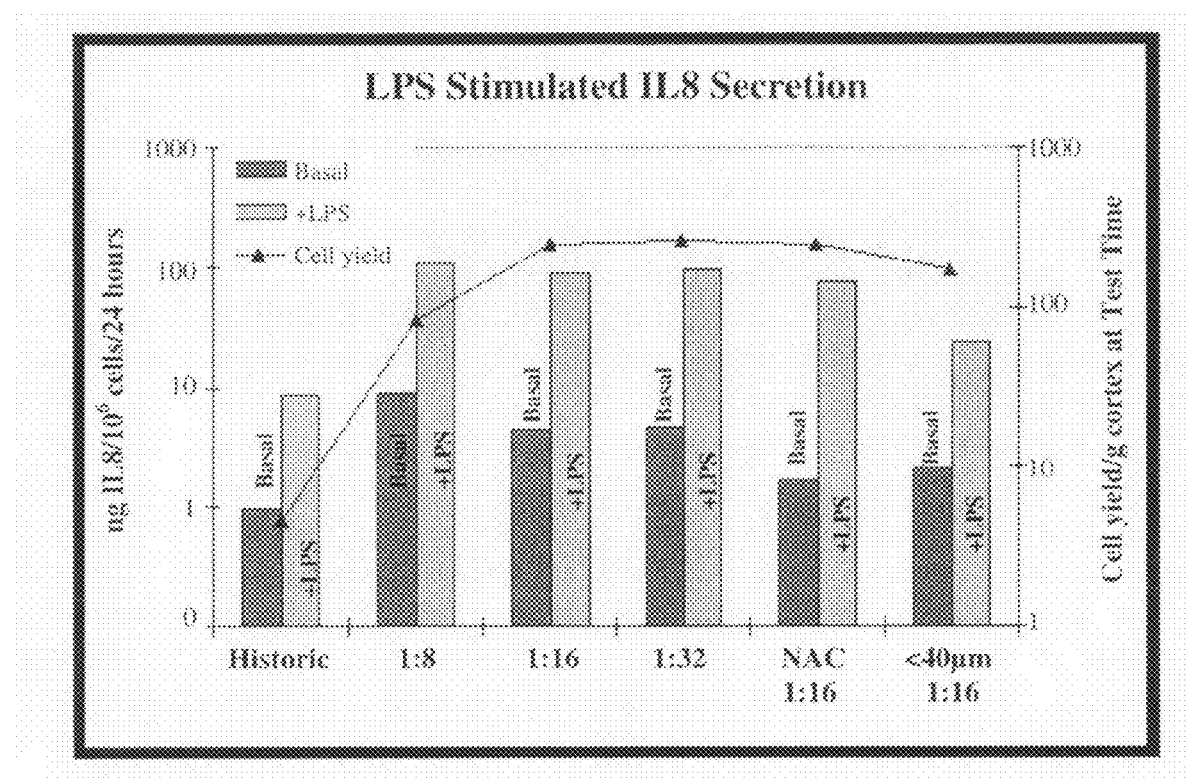
FIG. 9 is a histogram showing cytokine (IL-8) secretion by selected porcine enhanced propagation cell populations compared to historic method cell populations.

Secretion of IL-8, an important mediator in the innate immune system, is stimulated by LPS through toll-like receptors known to be present in epithelial cells. Additionally, basal secretion of IL-8 has been approved by the FDA as a measure of efficacy for release of human RAD used during Phase I/II clinical trials. Therefore, IL-8 secretion, both basal and stimulated by 10 μg/mL LPS challenge, was evaluated using a porcine-specific IL-8 Elisa kit (R&D Systems). Comparison of historic method cell populations and all enhanced propagation cell populations revealed a nearly 10 fold greater IL-8 secretion level for stimulated conditions as compared to basal conditions for both historic and EP population cells. Within the enhanced propagation conditions, altering initial plating density (1:8, 1:16 and 1:32) did not alter IL-8 secretion. Non-adherent cells (NAC) (discarded using historic protocols) and cell populations created from digestion of tissue to sizes under 40 μm ("<40 μm") were also similar (FIG. 9). Cultures are ongoing, so yield comparisons at time of testing are included as a reference.

(7) Conclusions

Application of enhanced REC propagation techniques to a porcine kidney model yielded more than 732 times more cells than historic propagation methods after only 6 weeks of culture. Previously excluded NAC cell populations retained all REC characteristics tested and may further advance cell yield. Studies indicate that yield increase is due to the stimulation of a transient amplifying precursor pool that persists in the adult kidney. Maintenance of this precursor pool in an undifferentiated state followed by the addition of RA at confluent density resulted in a morphologically correct renal epithelial cell population that retained physiologic therapeutic potential as measured by γGT enzyme activity and IL-8 secretion rates. Historic manufacturing practices yield 5 to 10 devices per kidney isolate, with the maximum production of 100,000 RAD annually. Continuation of this porcine REC enhanced propagation culture, shown in FIG. 10, resulted in an increase in yield by almost eight orders of magnitude over the historical method. This translated into an increase in cell doubling by more than 23 fold and also could translate into the construction of 2,546,000,000 devices (FIG. 10). It is contemplated that successful application of EP methods of the invention to the human system should increase manufacturing potential by at least three orders of magnitude, allowing for the construction of 10,000 units per isolation or 100,000,000 devices annually.

Example 2

This Example shows application of enhanced propagation techniques according to the invention to human RECs (HRECs) and the improved outcome of these techniques. More specifically, the Example describes (1) application of the enhanced propagation techniques to increase REC yield from human kidneys; (2) evaluation of the equivalence of HRECs obtained using the historic method and those obtained using enhanced propagation techniques according to the invention; (3) evaluation of the effects of cryopreservation on HREC identity and yield; and (4) integration of cryopreserved HREC obtained using enhanced propagation techniques according to the invention into a Bioartificial Renal Epithelial Cell System (BRECS), a type of WEB AK device.

(1) Parameters to Enhance REC Yield from Human Kidneys

Rationale:

The historic isolation protocol for REC is focused on the maintenance of fully differentiated epithelial sheets and greatly sacrifices the proliferation potential of isolated cells. Derived from intact cortex aggregates up to 600 μm in size, non-adherent particles are aspirated after 24 hours, removing a large REC precursor pool, and the renal tubule cell differentiation factor, retinoic acid (RA), is added at confluence. Propagation of cells cultured in this environment are limited by contact inhibition and does not take advantage of the inverse relationship between differentiation and proliferative potential. Application of enhanced propagation (EP) techniques according to the invention that include disruption of the tubular structure by more efficient enzymatic digestion, decreasing aggregate size, dilute plating ratios (both initial plating density and passage ratio), and removal of the differentiating factor, retinoic acid, from precursor cultures are demonstrated to a dramatic positive effect on cell yields.

Research Plan Overview:

Tissues are highly variable in age, disease state and time from procurement to isolation. Hence, the isolation of REC from at least six donors was chosen to assess the overall proliferative potential of tissues obtained. The isolation schedule consisted of two in the first month and approximately one every five weeks during the first six months of the project. When the effect of cryopreservation was to be tested, cryopreservation of cells at first subculture was performed and was followed by the prolonged expansion of both freshly isolated and reconstituted cryopreserved cells.

Kidney cortex tissue from each of six individual donors were minced and split into two equivalent units and processed using both historical and enhanced propagation protocols. A complete description of the protocols appear in Table 1, and are the same protocols as those used with porcine cells in Example 1. Slurry obtained from the more efficient digestion was further fractionated to establish the desired particle size threshold. At primary plating, fractionated cells were further subdivided to evaluate the effects of plating density and dilute passage ratio on yields. Culture was continued on selected populations showing the greatest potential for expansion. Cell yields from enhanced propagation were compared to yields from historical methods and evaluated in the context of supplying biomass necessary for projected ARF and ESRD therapies. A cell yield range per donor kidney was established that can be used to directly evaluate feasibility of device manufacture. It should be understood that the EP protocol shown in Table 1 is one embodiment of the invention. As shown in the experiments below, variations of the conditions shown in Table 1 also are useful to enhance cell yield.

Tissue Procurement:

Human cadaver kidneys were procured from the National Disease Research Interchange (NDRI). These kidney transplant discards, rejected for organ transplantation due to anatomic or fibrotic defect, were subjected to further screening on an individual basis to exclude unsuitable donors. Tissue was accepted from adults less than 80 years of age that tested negative for adventitious viruses, was not septic, had normal creatinine and blood urea nitrogen levels and no other indices of kidney disease. The ability to incite tissue processing 36 hours post cross clamp also was required. As the procurement agency, NDRI maintained all necessary records regarding donor identification. Tissue was simultaneously processed using historic protocols and using enhanced propagation protocols.

Enzymatic Digestion:

Kidneys were dissected clean of all external tissue and fat; the capsule discarded; and cortex excised from medulla. Cortex was minced with a sharp blade to a fine paste and digested at 1 g/mL in prewarmed collagenase/DNase (0.239 Wunchst units and 250 Kunitz units/mL) at 37° C. for 20 minutes. Using the historical protocol, the digestion was quenched with cold DMEM and passed through an 850 μm sieve. The population more than 850 μm was returned to the digestion flask and cycles were repeated until most tissue was less than 850 μm in size. The resulting slurry was subsequently fractionated over 710 and 600 μm sieves without further enzymatic digestion and remaining tissue aggregates greater than 600 μm were discarded. Cells were washed by centrifugation at 50×(g). Using the enhanced propagation protocol, a more efficient digestion process was accomplished by the substitution of Liberase Blendzyme 1 (available from Roche Applied Science, Germany) for collagenase at an equivalent activity and further disruption of tubular structure by digestion to a much smaller particle size. Liberase Blendzyme 1 is well characterized and has been specifically designed for tissue dissociation and eliminates the need for collagenase lot testing. If Liberase Blendzyme 1 is unavailable, a suitable collagenase IV can be used. The enzymatic digestion was not quenched with cold DMEM between digestion rounds but was kept warm with only the sieved filtrate being quenched as it passes into the collection beaker containing cold DMEM. This allowed the digestion to proceed uninterrupted. Aggregate sizes ranging from 212-150 μm, less than 150 to 90 μm, less than 90 to 38 μm, and less than 38 μm (single cell) were tested and evaluated for effects on cell yield. Cells were washed prior to plating by centrifugation at 300×(g) to create the pelleted slurry, which was inclusive of single cells and cell aggregates.

Figure 12:
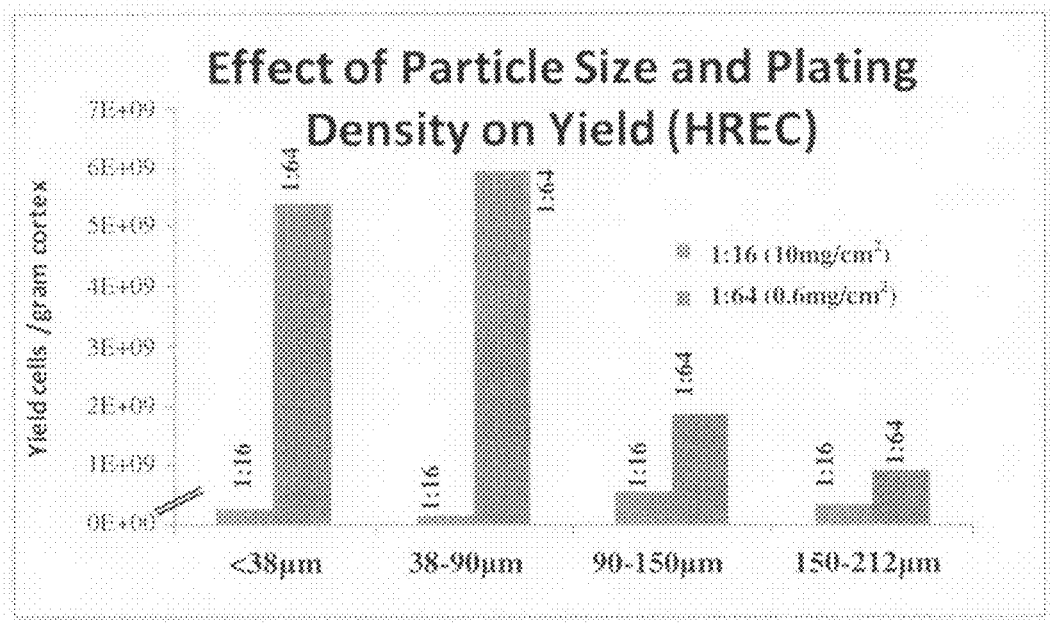
FIG. 12 is a histogram showing the effect of particle size and plating density on cell yield for human REC.

The effect of particle size and plating density on cell yield is shown in FIG. 12. Cell yield from the smaller fragments (e.g., less than 90 μm and less than 38 μm) was almost six times more than the other fractions tested, indicating that smaller particles created by more efficient enzymatic digestion had a positive impact on cell yield. In addition, more dilute plating (plating density) also enhanced yield. EP cultures with an initial dilution of 1:64 consistently displayed higher cell yield than EP cultures with an initial dilution of 1:16. This data is consistent with data generated using porcine cells. Additionally, all fractions under 212 μm appeared to contribute to the final yield.

Primary Plating:

For both the historical and EP methods, initial cell plating density was determined by estimating cell pellet size which inherently had different cell density due to the different g force used for centrifugation. However, for direct comparison, the cell yield was calculated per gram of cortex and per donor kidney. For both methods, cells were cultured in UltraMDCK Media (Lonza) supplemented with ½× the manufacturer's recommended dilution for insulin, transferrin, ethanolamine and selenium (ITES) supplement, 60 ng/L epidermal growth factor (EGF), $10^{-9}$ M triiodothyronine (T3) and 1× penicillin-streptomycin. Standard plating density was ½ mL (500 mg) of 50×(g) pellet/12 mL/100 mm plate and non-adherent fraction was aspirated after 24 hours in culture. Initial plating density was evaluated over a wide range by dilution of the 300×(g) pellet from $½^3$ (1:8) by orders of 2 to $½^9$ (1:512). To retain inherently expressed growth factors, only 50% of media was changed on an as needed basis. The need for media change was assessed by monitoring glucose, lactate and pH of culture media.

Figure 11:
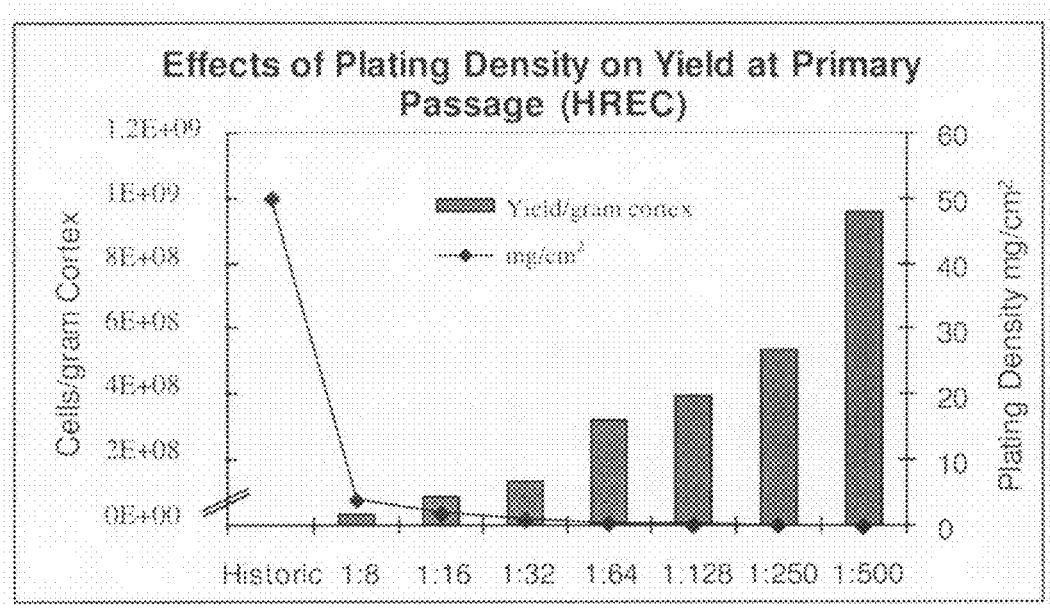
FIG. 11 is a histogram showing the effect of plating density on cell yield at primary passage for human REC. The historic method yield was $2.53 \times 10^6$ cells/gram cortex and is not shown on the graph due to scale.

The effect of plating density on cell yield is shown in FIG. 11. Similar to results obtained from porcine cells, plating density had a profound effect on cell yield. EP culture with initial dilution of 1:500 exhibited ten fold higher cell yield than EP cultures with initial dilution of 1:8 (which itself was greater than historic method results of $2.53 \times 10^6$ cells/gram cortex).

Sub-Culture:

For both the historic and EP methods, sub-culture was accomplished as follows. Cells were rinsed free of divalent cations. Subsequently, cells were enzymatically released from plates with 0.05% Trypsin-versene (Lonza) by incubation for 20 minutes at room temperature. Reaction was inhibited by 0.1% soybean trypsin inhibitor (Gibco). Upon reaching tight confluence, retinoic acid (RA) was added to cultures according to historic method 24 hours before passage at 1:2 and tested at the fifth passage. Cultures remained in RA supplemented media for the duration of the study and continued to be passaged at 1:2 while maintaining confluency between 50 and 100%. Enhanced propagation cultures did not receive RA at confluence and were sub-cultured at $10^5$ cells/mL, 12 mL/100 mm plate and passaged when 50-75% confluent, while maintaining confluency between 6.25 and 75%. All non-adherent cells from the media and rinses were retained and included in the sub-culture passage with the enzymatically released adherent cells from the corresponding plates.

Figure 13:
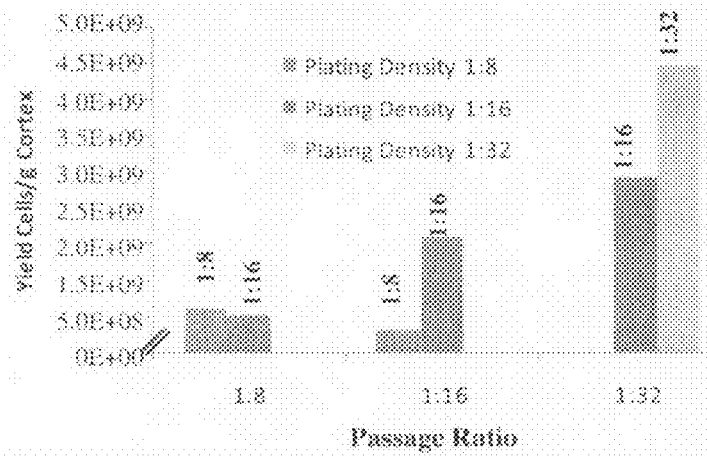
FIG. 13 is a histogram showing the effect of passage ratio on cell yield through second pass for human REC. Plating density refers to the initial plating after isolation.

As shown in FIG. 13, increasing subculture dilution (passage ratio) enhanced cell yield. EP culture with an initial plating density of 1:32, and subsequently subcultured at 1:32, yielded a greater number of cells than EP cultures with an initial density of 1:32 and subcultured at either the 1:8 or 1:16 ratio. Similarly, EP culture with an initial plating density of 1:16 and subsequently subcultured at 1:32 exhibited higher cell yield than those subcultured at lower dilutions. The studies using an initial plating density of 1:8 were terminated earlier than were the studies using an initial plating density of 1:16. It is contemplated that the results for an initial plating density of 1:8 would have shown greater cell yield than shown in FIG. 13 had the experiment reached conclusion. This observation suggests that in the context of manufacturing, greater cell yield may be achieved through less cell manipulation.

Figure 14:
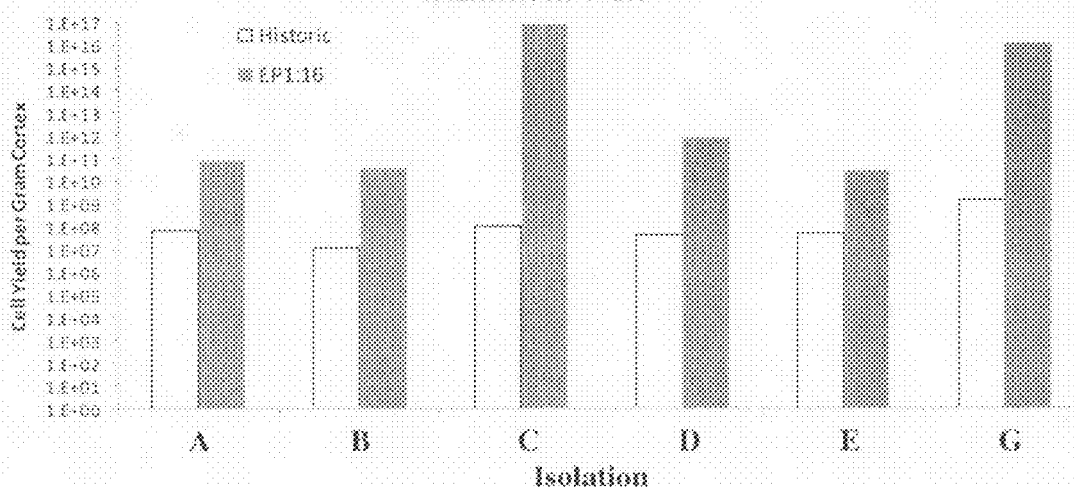
FIG. 14 is a histogram showing the actual cell yield from human REC propagated using the enhanced propagation method of the invention compared to the historic method. Samples A-E are human REC from five individual donors (as shown in FIG. 24). Sample G is a porcine REC (as shown in FIG. 10). The histogram is in a log scale.
Figure 15:
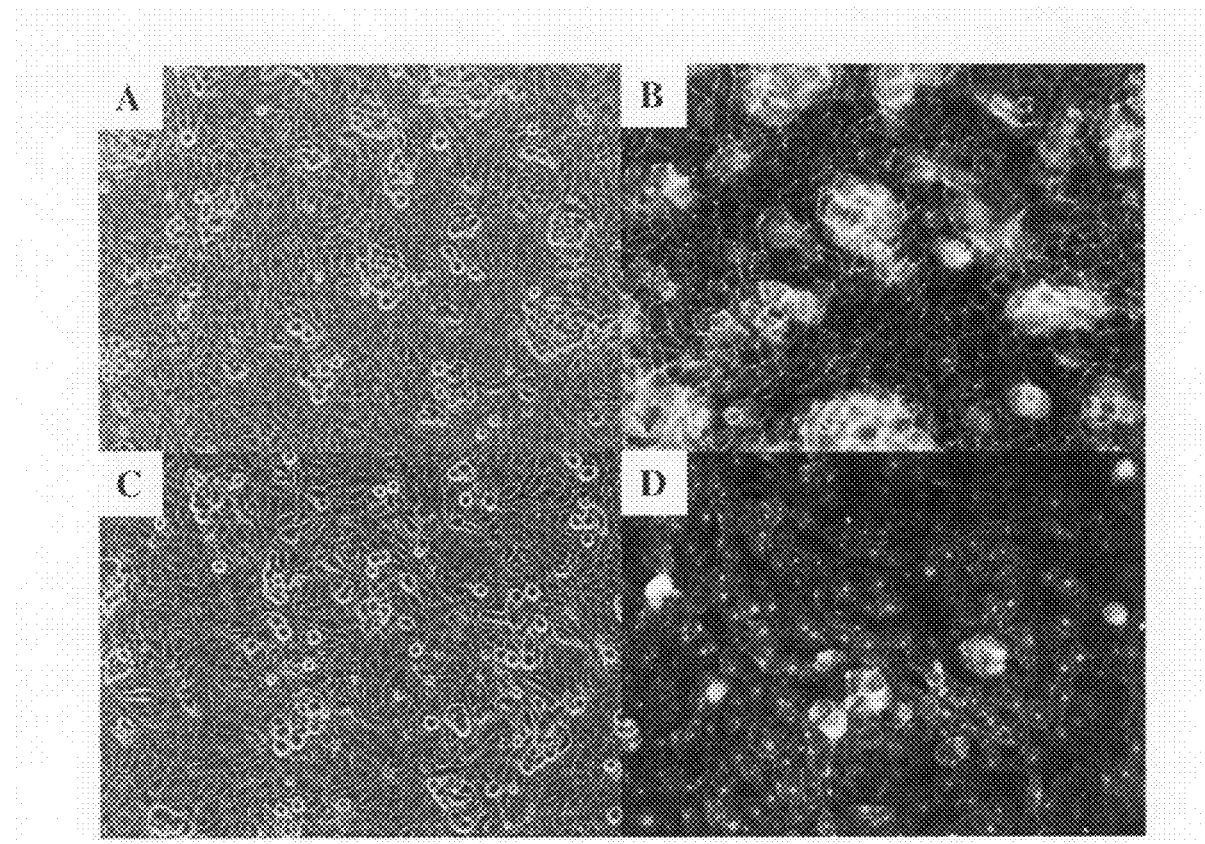
FIGS. 15A-D are photographs showing epithelial monolayers derived from cryopreserved human REC as compared to freshly isolated human REC propagated using the enhanced propagation method of the invention. Phase contrast photographs of passage 5 monolayers are shown on the left (FIGS. 15A and 15C). Immunohistochemistry of AT-1 and ZO-1 are on the right (FIGS. 15B and 15D). Fresh cells are represented in the top rows (FIGS. 15A and 15B). Cells reconstituted from frozen stocks are shown on the bottom rows (FIGS. 15C and 15D).

Cell Yield:

The maximum cell yield from EP methods according to the invention compared to the historic method is shown in FIG. 14 and summarized in FIG. 24. Trials were conducted using human REC from five different donors (A-E). As expected, the overall cell yield was different for each donor. Typically, healthy kidneys (e.g., from a healthy individual) produced a greater cell yield than unhealthy kidneys (e.g., from an unhealthy individual). However, application of the EP method enhanced cell yield by 4-9 orders of magnitude in all the donor cells tested relative to application of historic methods (FIG. 14; Note the logarithmic scale). This increase translated into an increase of approximately 9-30 cell doublings (FIG. 24). Similarly, in a trial using porcine REC (sample G), the cell yield was increased by 8 orders of magnitude when the EP method according to the invention was used relative to application of the historic method. Further, the cell yield from EP methods according to the invention translates into the construction of from 16,000 to almost 81,000,000,000 devices (FIG. 24). Hence, the EP method consistently enhances cell yield despite donor variations or species variations.

(2) Equivalence of Human REC Obtained by Historic Method and Those Obtained by Enhanced REC Progenitor Propagation Protocols Rationale:

The characteristics of primary cell cultures can migrate upon continuous subculture. In order to ascertain the continued therapeutic potential of cultures, populations were allowed to differentiate and were then assayed to ascertain cell identity and retention of therapeutic qualities.

Research Plan Overview:

Tissues were equally split and subjected to both historical and enhanced propagation protocols (Table 1). Progenitor populations derived from enhanced propagation were seeded at confluent density and terminally differentiated by both contact inhibition and the addition of retinoic acid. Cells were assayed for the ability to form polarized renal epithelium using antibodies to acetylated tubulin, zona occludens and γ-glutamyltranspeptidase to reveal apical central cilia, tight junctions and a representative brush border enzyme, respectively. Endotoxin stimulation assays assessed retention of cytokine reactivity by measuring basal IL-8 secretion levels and levels post LPS challenge. γGT enzyme assay complemented immunohistochemical results and demonstrated that γGT is functionally active and that cells retain the ability to respond to oxidative stress. Cells were tested minimally at 7 additional doublings ($2e^7$=128× more cells) and 10 additional doublings ($2e^{10}$=1024× more cells) as compared to populations obtained from historic protocols.

For all tests, cells were passaged and seeded at confluent density, $10^6$ cells/mL/5 $cm^2$. After 2 days in culture, RA was added to media and cells were cultured for an additional 5 days.

Oxidative Stress Response:

For immunotyping and assay for γGT activity, cells were seeded onto 8 well chamber slides while 12 well culture plates were used for testing cytokine response. Qualitative assessments of γGT activity in living cells were determined by the method of Rutenberg (Rutenberg et al. (1968), J. HISTO. CYTO. 17(8):517-526) after which slides were fixed in 4% paraformaldehyde permeated with 0.1% TritonX-100 and subsequently labeled with antibodies to REC specific markers (Table 2).

TABLE 2

Antibodies for Identification of Renal Epithelial Cells

| Antibody/Antigen/Manufacturer | Abbreviation | Detection | Localization |
|---|---|---|---|
| Rabbit anti-human Zona-Occludens-1 (Zymed) | ZO-1 | Anti-rabbit IgG AlexaFluor 488 | Epithelial Tight Junctions |
| Mouse anti-human Acetylated Tubulin (Zymed) | AT-1 | Anti-mouse IgG AlexaFluor 594 | Apical central Cilia of proximal tubule cell (PTC) |
| Mouse anti-human γ-Glutamyltranspeptidase (BioVision) Counterstain | γGT | Anti-mouse IgG AlexaFluor 594 | Brush Border PTC |
| 2-(4-amidinophenyl)-6-indolecarbamidine dihydrochloride | DAPI | NA | Nuclei |

Figure 16:
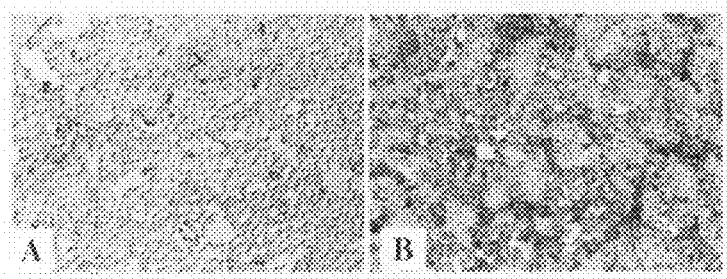
FIGS. 16A and 16B are photographs showing the γGT activity of human REC propagated using the enhanced propagation method of the invention. Activity was detected in the most advanced enhanced propagation cell populations from an initial 1:16 plating density and 1:16 passage ratio after four passages.

As shown in FIG. 16, γGT was functionally active in advanced human EP cell populations. EP cell population initially plated at 1:16 dilutions and subsequently passaged at 1:16 ratio retained the ability to ameliorate oxidative stress as indicated by its ability to catalyze the recovery of glutathione. This indicates that EP cells retained therapeutic potential as measured by its γGT activity.

Cytokine Response:

The evaluation of cytokine response was carried out as follows. Cells were rinsed and refilled with 1 mL growth media supplemented with 0.1% bovine serum albumin both with and without 10 μg/mL lipopolysaccharide (LPS). After 24 hours, supernatants were removed and clarified by centrifugation, and then the concentration of IL-8 was determined using a human specific ELISA kit (Quantikine ELISA kit R&D systems). Cells derived from enhanced propagation techniques were repetitively tested as the cultures progressed, specifically at time points approximating 100×, 250×, 500×, and, if applicable, over 1000× historic yield. Comparisons were made between progressing EP cells while those generated using historic protocols were tested only at fifth passage, the point at which historic populations were integrated into devices for clinical studies.

Figure 17:
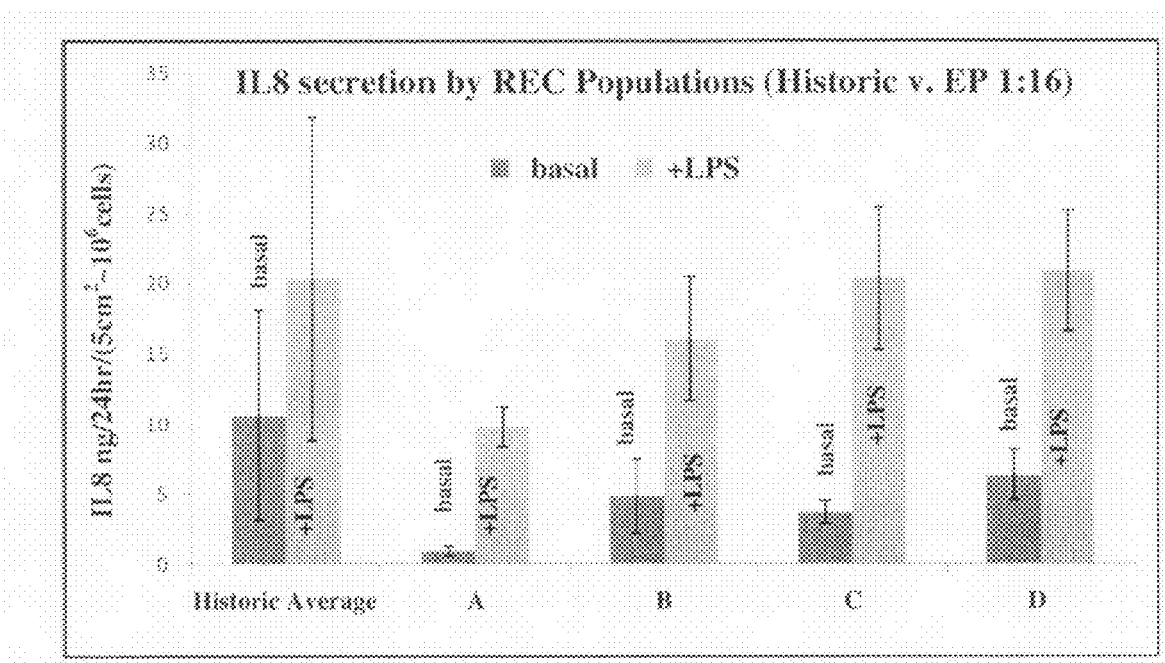
FIG. 17 is a histogram showing cytokine (IL-8) secretion by selected human enhanced propgation cell populations (samples A-D as shown in FIG. 24) compared to a historic method cell population average.

FIG. 17 shows IL-8 secretion by human REC populations cultured using the historic or EP methods. LPS stimulation resulted in a 4-5 fold increase in IL-8 secretion as compared to basal levels for both historic and EP cell populations initially plated at 1:16 and subcultured at a 1:16 ratio. This result indicates that human REC populations cultured using the EP method retained physiologic therapeutic potential, as measured by their IL-8 secretion rates.

(3) Evaluation of Effect of Cryopreservation on REC Identity and Yield.

Rationale:

A manufacturing stop point allows for all required biologics testing to be completed prior to the incorporation of inappropriate tissue into a therapeutic biological device. Also, inclusion of a manufacturing stop point allows for continuity of device manufacture even though kidney donor availability is intermittent. Cryostorage of REC precursors provides the required stop point, but has the potential to reduce cell viability and amplification potential. Accordingly, the effect of cryopreservation on REC precursors was evaluated.

Research Plan Overview:

Isolates were cryopreserved on first passage using serum free cryopreservation solutions, consisting of growth media without retinoic acid and 10% DMSO. REC progenitors were subsequently thawed and subjected to matched enhanced propagation culture protocol parameters shown to maximize yields of differentiated REC (Table 1). Cell yield and retention of REC characteristics were evaluated in REC monolayer culture as described above, and compared to data obtained for fresh isolates.

Cryopreservation:

Cells were cryopreserved at first passage after being cultured according to the enhanced propagation methods of the invention (Table 1). Trypsinized cells were mixed at $10^7$ cells/mL with cryoprotectant, placed in a manual, controlled rate freezing apparatus (Mr. Frosty) at −80° C. overnight and then transferred to the vapor phase of liquid nitrogen. Cells remained frozen for at least 2 weeks prior to use in cryopreservation studies. For use, cells were quickly thawed followed by the slow dilution of cryoprotectant and removal of this solution by centrifugation. Cells were plated at a 1:16 dilution according to the EP methods of the invention and were maintained under EP conditions until seeding at confluent density for characterization studies or integration into a biotherapeutic device. Retinoic acid was added after 48 hours post seeding for the characterization studies and 5-7 days post seeding for the biotherapeutic device studies, allowing for maximal coverage prior to differentiation.

Morphology:

Freshly isolated human REC or cryopreserved human REC were propagated using EP methods. Passage of fresh or reconstituted frozen stocks at a confluent density resulted in the formation of a monolayer with typical cobblestone morphology. Characteristics associated with polarized epithelium were evident in the human REC culture by the punctate AT-1 positive staining indicative of centralized cilia and ZO-1 positive staining indicative of epithelial tight junction (FIGS. 15A-D). Hence, propagation of reconstituted human REC precursor cells in an undifferentiated state followed by RA induced differentiation resulted in morphologically correct renal epithelial cells in both fresh and frozen conditions.

Figure 18:
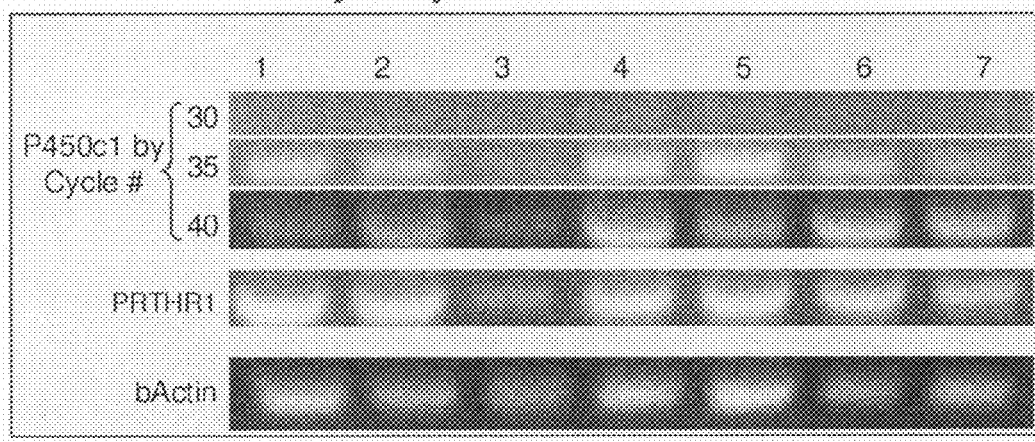
FIG. 18 shows the expression of 1-alpha hydroxylase in cryopreserved human REC propagated using the enhanced propagation method of the invention. As shown in the table, cryopreserved human REC was cultured in media containing PTH, cAMP, or forskolin. 1-alpha hydroxylase expression was detected by RT-PCR in all the samples tested.

1-Alpha Hydroxylase Expression:

Vitamin D metabolism is an important hormonal function of human REC. Specifically, the mitochondrial enzyme 1-alpha hydroxylase converts the inactive 25-hydroxyvitamin $D_3$ to the active 1,25-dihydroxyvitamin $D_3$ in the kidney. The activity of 1-alpha hydroxylase in cryopreserved human REC cells was confirmed by determining 1-alpha hydroxylase expression in the cells using RT-PCR. Cryopreserved human REC cells were propagated under EP methods of the invention in the presence of parathyroid hormone (PTH), cAMP, or forskolin. PTH and forskolin increase cAMP cellular levels which, in turn, induce 1-alpha hydroxylase expression. cDNA was extracted from the cells, and RT-PCR was performed to determine 1-alpha hydroxylase expression. As illustrated in FIG. 18, 1-alpha hydroxylase expression was confirmed in all of the reconstituted human REC samples propagated under EP methods of the invention, suggesting that these cells retain 1-alpha hydroxylase activity following cryopreservation.

(4) Integration of Cryopreserved Human REC Derived from EP Protocols into a Bioartificial Renal Epithelial Cell System (BRECS):

Rationale:

Carbon disks carrying REC constitute the living component of a BRECS (for example, as described in U.S. Patent Publication No. 2009-0081296), a representative type of WEBAK. The ability to fabricate these constructs using cryopreserved human cells derived from EP methods according to the invention demonstrated manufacturing feasibility. Metabolic parameters can be used to determine biomass per disk, which are then be used to estimate the biotherapeutic potential per device and per donor kidney.

Research Plan Overview:

After thawing and expanding (using EP methods according to the invention) previously cryopreserved cells (which were propagated under EP methods according to the invention up to the point of cryopreservation) from separate donors, the resulting cells were seeded onto carbon disks and cultured directly in BRECS units. Parallel monolayer cultures with known surface area, biomass and cell number were seeded. Metabolism was monitored by oxygen and glucose consumption and lactate production. Values calculated from monolayer cultures were then used to extrapolate the cell-covered surface area, biomass and cell number in the disks. At 2.5 weeks, 5 weeks, 9 weeks, and 11 weeks of BRECS culture, human REC containing carbon disks were fixed and coverage was evaluated by histology.

Integration of Advanced EP Populations into a BRECS:

Cryopreserved cells were seeded post recovery onto porous and trabeculated carbon, niobium-coated disks that constitute the REC-containing biotherapeutic component of the BRECS, a representative type of WEBAK. Cells were seeded by static drop-wise loading of a 75 µL cell suspension in growth media containing $10^6$ cells onto a single disk side followed by 1.5 hour incubation at 37° C. Thereafter, the disk was rotated 180°, which was followed by seeding the opposite side of the disk. Up to 20 cell carrying disks can be cultured per BRECS with 250 mL of media in a recirculating perfusion circuit, at perfusion rates between 10-100 mL/minute. For metabolic assessment of disks, parallel monolayer cultures were created for comparison. Retinoic acid was added after cell growth rate had plateaued, typically at 5-7 days, and supernatant samples taken over the life of the cultures. Changes in glucose and lactate concentrations were determined using commercially available colorimetric kits and used to calculate the glucose consumption and lactate production rates. Rates were compared between the monolayer of known biomass and the disk culture system to estimate the biomass retained within the disks. After 2.5 weeks, 5 weeks, 9 weeks, or 11 weeks, disks were fixed with 4% paraformaldehyde permeated with 0.1% TritonX-100, and cells were subsequently labeled with DAPI to evaluate cell coverage.

Figure 19:
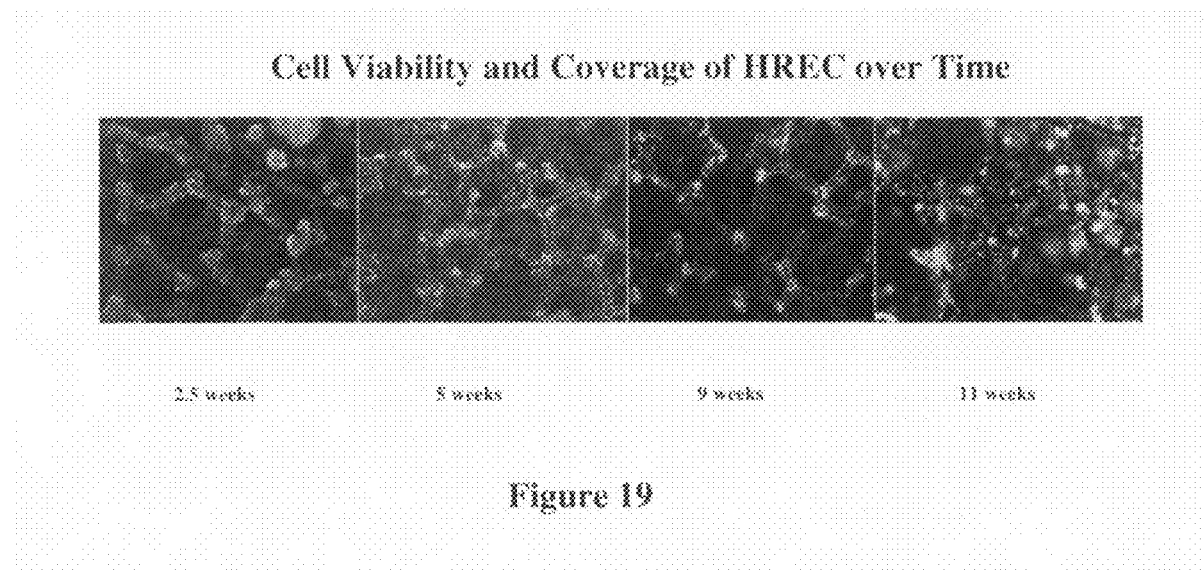
FIG. 19 is a series of photographs showing the cell viability of cryopreserved human REC seeded on carbon porous, trabeculated disks coated with niobium during the course of 11 weeks.

Cell Viability:

Cryopreserved human REC were reconstituted and seeded onto carbon niobium disks. FIG. 19 shows the viability of these cells over a period of 11 weeks as measured by DAPI staining. No significant differences in DAPI staining were observed between reconstituted cells seeded onto the disks for 2.5 weeks, 5 weeks, 9 weeks, or 11 weeks, indicating that these cells maintain their viability over time.

Figure 20:
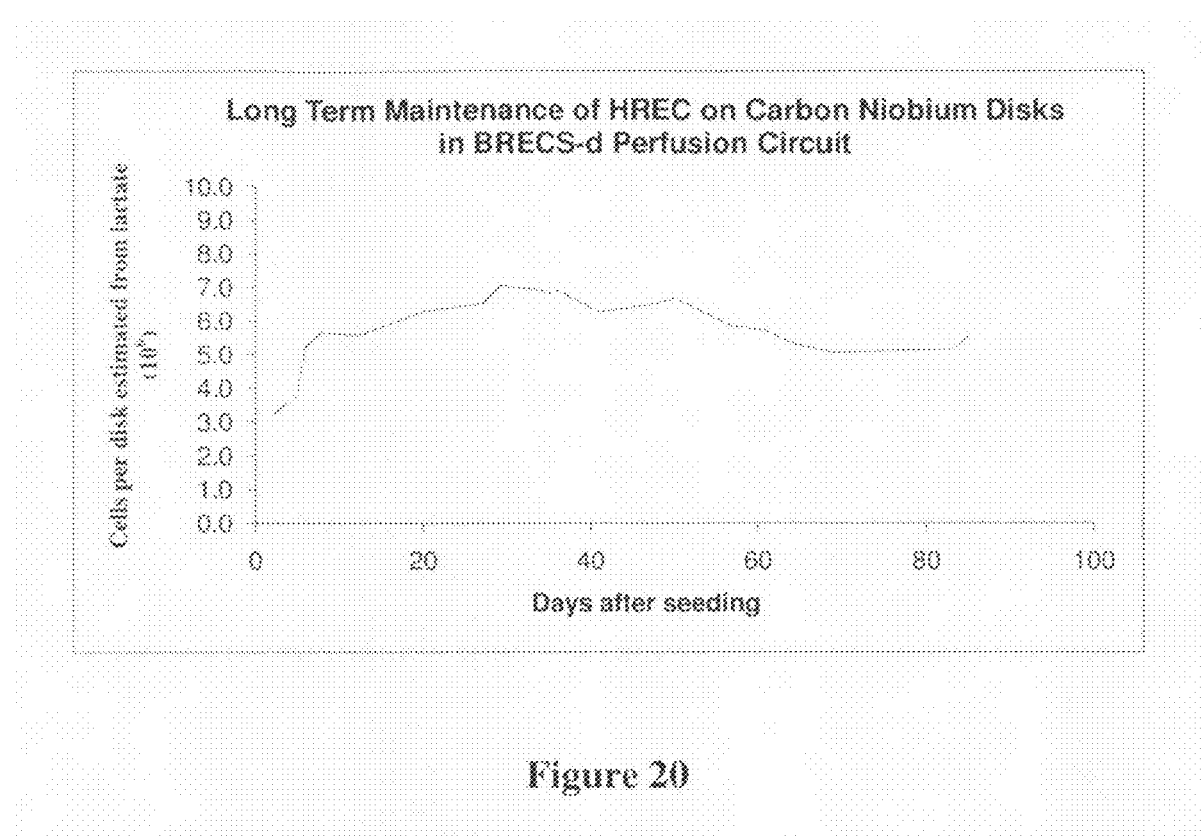
FIG. 20 is a line graph showing the lactate production of cryopreserved human REC seeded on carbon niobium disks during the course of over 80 days.

The viability and metabolic activity of cryopreserved human REC cells seeded onto carbon niobium disks were also determined by measuring lactate production. Lactate production was measured over a period of about 80 days. As shown in FIG. 20, reconstituted human REC cells continued to produce lactate over a period of 80 days, indicating that these cells remain viable and metabolically active following incorporation into the BRECS device.

Figure 22:
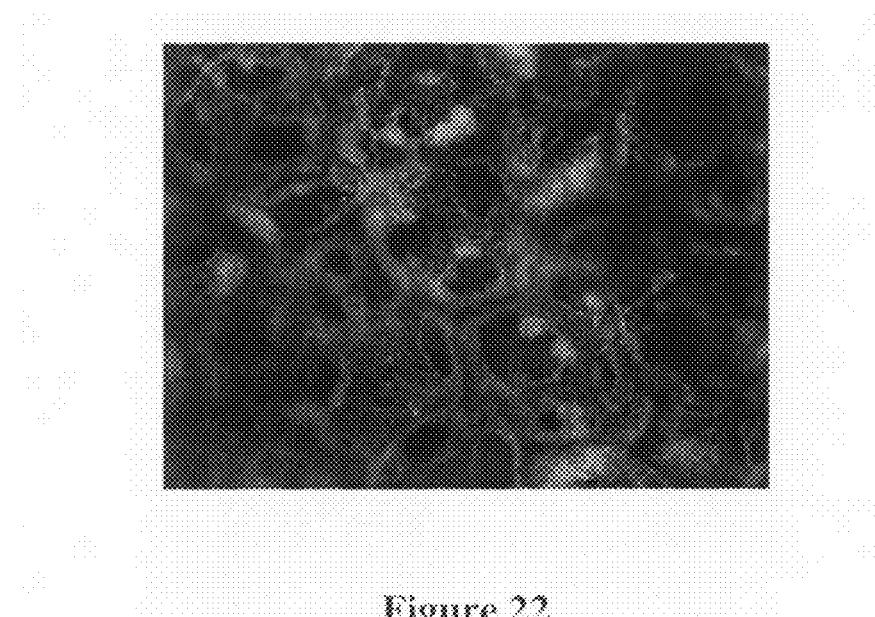
FIG. 22 is a photograph showing human REC cell viability on carbon niobium disks incorporated into a BRECS device and maintained using a peritoneal dialysis perfusion circuit.

Cell viability on carbon niobium disks incorporated into BRECS and viability maintained using a peritoneal dialysis perfusion circuit were also determined. Using a sheep model of chronic renal failure, an animal was treated with a BRECS containing human cells after viability had been confirmed using lactate production and glutathione (GSH) metabolism. After the completion of the peritoneal dialysis animal study, one disk was removed from the 20 disk unit for analysis of cell coverage and viability by DAPI. The remaining 19 disks were placed immediately into an in vitro perfusion circuit containing GSH media. A sample was taken 1 hour later to evaluate glutathione metabolism. Before placement in the peritoneal dialysis circuit, the calculated cell number per disk, as evaluated by GSH metabolism rates, was $0.467 \times 10^6$ and after 48 hours it was $0.478 \times 10^6$. The persistence of glutathione metabolism along with the extensive viable cell coverage as revealed by DAPI staining (FIG. 22) indicates that cells remained viable within the cartridge during therapy.

Figure 21:
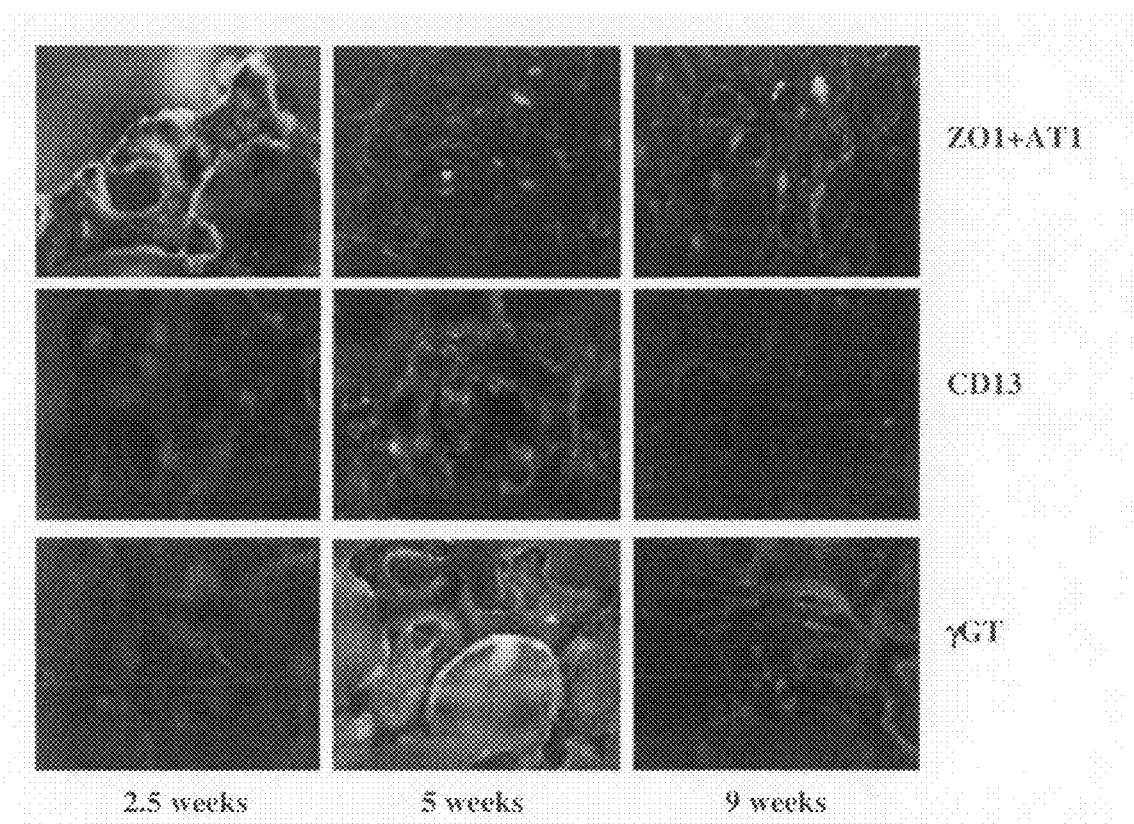
FIG. 21 is a group of photographs showing the morphology of cryopreserved human REC seeded on carbon niobium disks. Immunohistochemistry was performed using ZO-1, AT-1, and γGT antibodies. Photographs were taken with 10× objective.

Morphology:

Reconstituted human RECs seeded onto carbon niobium disks were assayed for the ability to form polarized renal epithelium using antibodies to acetylated tubulin (AT-1) and zona occludens (ZO-1) to reveal apical central cilia and tight junctions. Aminopeptidase-N(CD13), a brush border enzyme that facilitates $Na^+$ dependent amino acid transport, and γ-glutamyltranspeptidase (γGT), a brush border enzyme that facilitates glutathione metabolism, also were assessed, with antibody staining being prominent along the entire disk surface (FIG. 21). These renal differentiation markers remained constant over the course of 9 weeks, indicating that reconstituted human REC maintained on carbon niobium disks can retain their ability to differentiate and form polarized renal epithelium over time.

Example 3

Cell therapy in chronic care situations may benefit from the use of autogenic cells, such that patient's own cells can be sampled, grown, and used in a therapeutic device used to treat that patient. This example demonstrates the feasibility of an autologous device manufactured for chronic applications using cells from a punch biopsy.

Punch Biopsy:

A punch biopsy procedure was used to demonstrate the feasibility of autologous device manufacture for chronic applications using diseased kidney. Kidney tissue biopsies are routinely performed to aid in the diagnosis of renal disease. It follows that if the improved cell yield demonstrated using cells obtained from whole kidney and using EP methods according to the invention can be applied to small biopsies, autologous devices may be manufactured. Typically, a 14-18 gauge biopsy needle is used to remove a 1 cm long core of tissue from the kidney for diagnosis. To mimic this procedure, a glass Pasteur pipet with a 1.2 mm diameter (equivalent to 16 gauge) was plunged through cortex of an excised human kidney transplant discard, removing a core of tissue 1 cm (l)×0.06 cm (r) (translating to 0113 $cm^3$ of tissue or 11.3 mg of tissue). Liberase blendzyme (0.239 Wunchst units/mL) containing 250 Kunitz units/mL DNase was used to treat the tissue at 37° C. for 30 minutes in shaking water bath, as in Table 1. Cells were passed through a 100 µm sieve into ice cold DMEM. The remainder was placed back in a vial, with 5 mL of fresh enzyme added, and returned to another digestion round. Slurry was collected into 50 mL conical tubes and washed by centrifugation at 300×g to generate pelleted slurry.

Each pellet from each digest was put into 20 mL of RA (retinoic acid) free media, which was UltraMDCK Media (Lonza) supplemented with ½× the manufacturer's recommended dilution for insulin, transferrin, ethanolamine and selenium (ITES) supplement, 60 ng/L epidermal growth factor (EGF), $10^{-9}$M triiodothyronine (T3) and 1× penicillin-streptomycin. Passage and continued growth proceeded according to the EP method as shown in Table 1, at an initial plating density of 0.15 mg cortex/$cm^2$ culture plate and passage ratios of 1:16, assuming confluent plate conditions (0.15 mg of kidney cortex yielded 0.55 µL of slurry).

Figure 23:
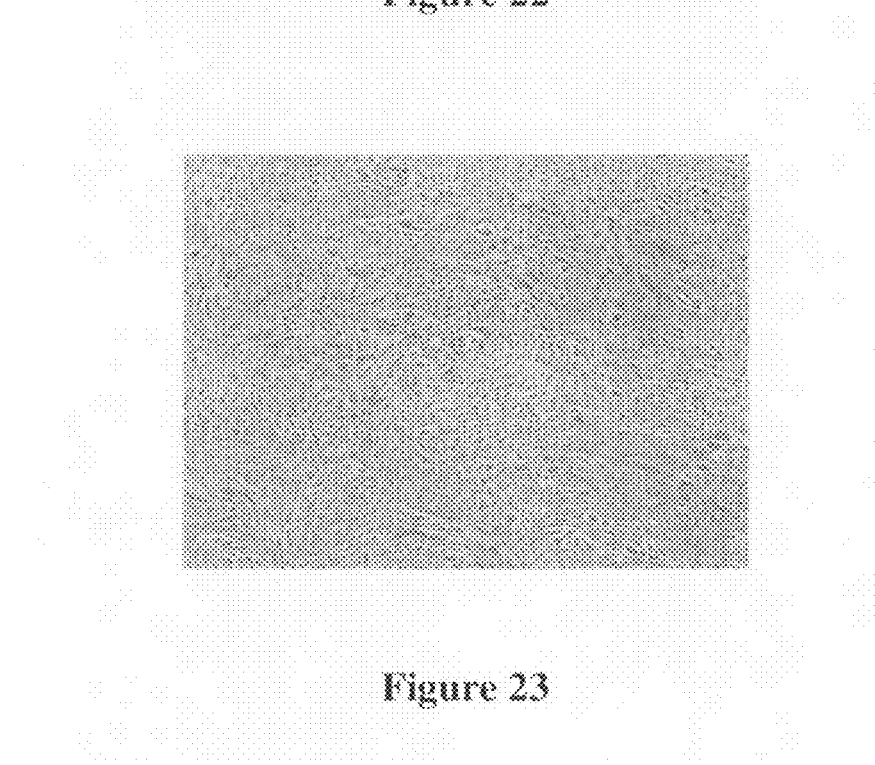
FIG. 23 is a photograph showing the morphology of human REC obtained from mimicked biopsy.

Yield calculations through five passages showed that at least one device can be seeded from one 11 mg biopsy after only six weeks of growth, thus feasibility was demonstrated (FIG. 24, Sample F). Yield is expected to increase with additional culture time. The resulting cells had the correct morphology (FIG. 23).

As described previously, historic manufacturing practices yield 5 to 10 devices per donor kidney, with the maximum production of 100,000 RAD annually. Application of EP methods resulted in significant enhancement of cell yield using human REC from five individual donors. As indicated in FIG. 24, this translates into the construction of 16,688 to 80,960,000,000 devices. It is contemplated that successful application of EP methods of the invention to the human system should dramatically increase manufacturing potential.

INCORPORATION BY REFERENCE

The entire disclosure of each of the publications, patent documents, and database references referred to herein is incorporated by reference in its entirety for all purposes to the same extent as if each individual source were individually denoted as being incorporated by reference.

EQUIVALENTS

The invention may be embodied in other specific forms without departing form the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method for enhanced propagation of cells from a kidney sample, the method comprising culturing renal precursor cells from the sample while retaining non-adherent cells when culture or subculture growth medium is changed, thereby to enhance propagation of a cell population from the sample.

2. The method of claim 1, wherein the method maintains the precursor cells in an undifferentiated state.

3. The method of claim 1, wherein the method increases the number of precursor cells relative to the number present in the sample.

4. The method of claim 1, wherein the method comprises dilution of cells in the sample.

5. The method of claim 1, wherein the enhanced propagation cell population comprises renal cells.

6. The method of claim 1, further comprising administering retinoic acid.

7. The method of claim 1, the method comprising applying conditions that stimulate precursor cells.

8. The method of claim 1, the method comprising applying conditions that amplify precursor cells.

9. A method for propagating renal cells from a kidney sample, the method comprising:
   (a) treating the kidney sample to produce tissue fragments having a dimension of about 212 μm or less in size;
   (b) harvesting at least a portion of the tissue fragments by centrifugation at greater than 200×(g) to produce a pelleted slurry;
   (c) applying a portion of the pelleted slurry produced in step (b) to a solid support and culturing the cells from the pelleted slurry in the absence of retinoic acid and under conditions to permit the renal cells to attach to the solid support and divide;
   (d) harvesting the cells produced in step (c) prior to reaching confluence on the solid support;
   (e) applying a portion of the cells harvested in step (d) to a solid support and subculturing the cells in the absence of retinoic acid and under conditions to permit the renal cells to attach to the solid support and divide; and
   (f) harvesting the cells produced in step (e) to produce a propagated population of renal cells.

10. The method of claim 9, wherein non-adherent cells are retained when culture or subculture growth medium is changed.

11. A method for enhanced propagation of cells from a kidney sample, the method comprising:
   separating the kidney sample into fragments of about 212 μm or less in size to produce a slurry;
   centrifuging the slurry at greater than 200×(g) to produce a pelleted slurry;
   creating a culture by applying to a growth surface about 10 μl or less of the pelleted slurry per square centimeter of surface area on which the culture is to be grown, wherein said 10 μl or less of the pelleted slurry is resuspended in a sufficient amount of a culture medium for plating; and
   subculturing about $8.7 \times 10^4$ or fewer cells from the culture per square centimeter of surface area on which the subculture is to be grown.

12. The method of claim 11, further comprising adding retinoic acid after the subculturing step.

13. The method of claim 11, wherein non-adherent cells are retained when culture or subculture growth medium is changed.

14. The method of claim 11, wherein the subculturing step occurs prior to confluence.

15. The method of claim 11, further comprising subculturing about $8.7 \times 10^4$ or fewer cells from the subculture per square centimeter of surface area on which the further subculture is to be grown.

16. The method of claim 9, wherein step (e) further comprises permitting the cells to divide until confluence.

17. The method of claim 16, wherein step (f) further comprises seeding harvested cells onto a solid support.

18. The method of claim 17, further comprising adding retinoic acid to the cells seeded onto the solid support and permitting the cells to differentiate.

19. The method of claim 9, wherein after step (f), the cell yield is at least $3.22 \times 10^{10}$ renal epithelial cells per gram of kidney cortex tissue.

20. The method of claim 9, wherein the kidney sample is an adult kidney sample.

21. The method of claim 11, wherein the kidney sample is an adult kidney sample.

* * * * *